(12) United States Patent
Kim et al.

(10) Patent No.: US 7,894,026 B2
(45) Date of Patent: Feb. 22, 2011

(54) THIN FILM TRANSISTOR ARRAY PANEL AND LIQUID CRYSTAL DISPLAY INCLUDING LIGHT SHIELD

(75) Inventors: Dong-Gyu Kim, Yongin-si (KR); Seung-Soo Baek, Seoul (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 161 days.

(21) Appl. No.: 10/954,281

(22) Filed: Oct. 1, 2004

(65) Prior Publication Data

US 2005/0110924 A1 May 26, 2005

(30) Foreign Application Priority Data

| Oct. 1, 2003 | (KR) | ................ 10-2003-0068172 |
| Feb. 19, 2004 | (KR) | ................ 10-2004-0011172 |
| Aug. 24, 2004 | (KR) | ................ 10-2004-0066755 |

(51) Int. Cl.
G02F 1/1333 (2006.01)
G02F 1/1343 (2006.01)
G02F 1/1335 (2006.01)

(52) U.S. Cl. .............. 349/111; 349/110; 349/38; 349/39; 349/139

(58) Field of Classification Search ............ 349/38–39, 349/139, 110, 111, 113
See application file for complete search history.

(56) References Cited

U.S. PATENT DOCUMENTS

| 5,414,547 A * | 5/1995 | Matsuo et al. ............. 349/44 |
| 5,777,701 A * | 7/1998 | Zhang ....................... 349/44 |
| 5,831,708 A * | 11/1998 | Hiraishi et al. ............ 349/143 |
| 5,953,088 A * | 9/1999 | Hanazawa et al. ......... 349/110 |
| 6,219,118 B1 * | 4/2001 | Zhang ....................... 349/110 |
| 6,255,130 B1 * | 7/2001 | Kim .......................... 438/30 |
| 6,278,131 B1 * | 8/2001 | Yamazaki et al. .......... 257/59 |
| 6,335,776 B1 * | 1/2002 | Kim et al. .................. 349/129 |
| 6,411,355 B1 * | 6/2002 | Manabe et al. ............ 349/120 |
| 6,816,222 B2 * | 11/2004 | Ono et al. .................. 349/143 |
| 6,831,623 B2 * | 12/2004 | Yasukawa .................. 345/90 |
| 2003/0090599 A1 * | 5/2003 | Ochiai et al. ............... 349/39 |
| 2003/0133055 A1 | 7/2003 | Um et al. |
| 2004/0119924 A1 | 6/2004 | Takeda et al. |
| 2006/0146241 A1 * | 7/2006 | Choi et al. ................. 349/129 |

FOREIGN PATENT DOCUMENTS

| CN | 1369731 | 9/2002 |
| CN | 1420393 A | 5/2003 |
| CN | 1420383 | 8/2003 |
| JP | 02-033031 U | 3/1990 |
| JP | 04-318512 | 11/1992 |
| JP | 5019293 A | 1/1993 |
| JP | 405019293 | * 1/1993 |
| JP | 05-127195 | 5/1993 |

(Continued)

*Primary Examiner*—Hoan C Nguyen
(74) *Attorney, Agent, or Firm*—Innovation Counsel LLP

(57) ABSTRACT

A thin film transistor array panel is provided, which includes: a gate line; a data line intersecting the gate line; a thin film transistor connected to the gate line and the data line; a pixel electrode connected to the thin film transistor; a passivation layer formed on the data line; and a shielding electrode overlapping the data line at least in part and electrically disconnected from the data line.

19 Claims, 28 Drawing Sheets

FOREIGN PATENT DOCUMENTS

| | | |
|---|---|---|
| JP | 06-250220 | 9/1994 |
| JP | 06-347827 | 12/1994 |
| JP | 10-039336 | 2/1998 |
| JP | 10-221715 | 8/1998 |
| JP | 11-242244 | 9/1999 |
| JP | 11-326927 | 11/1999 |
| JP | 2000-029059 | 1/2000 |
| JP | 2001-166321 | 6/2001 |
| JP | 2003-043489 | 2/2003 |
| JP | 2003-050386 | 2/2003 |
| JP | 2003084289 | 3/2003 |
| JP | 2003-287770 | 10/2003 |
| JP | 2003-322865 | 11/2003 |
| JP | 2004-085898 | 3/2004 |
| JP | 2004-094190 | 3/2004 |
| KR | 1999-006951 | 1/1999 |
| KR | 10-2000-0057973 A | 9/2000 |
| KR | 10-2000-0066397 A | 11/2000 |
| KR | 10-2001-0046651 A | 6/2001 |
| KR | 10-2001-0046653 A | 6/2001 |
| KR | 10-2002-0046559 A | 6/2002 |
| KR | 10-2002-0071542 A | 9/2002 |
| KR | 10-2003-0040025 A | 5/2003 |
| KR | 10-2003-0057682 A | 7/2003 |
| TW | 556848 | 10/2003 |
| TW | 200415421 | 8/2004 |

\* cited by examiner

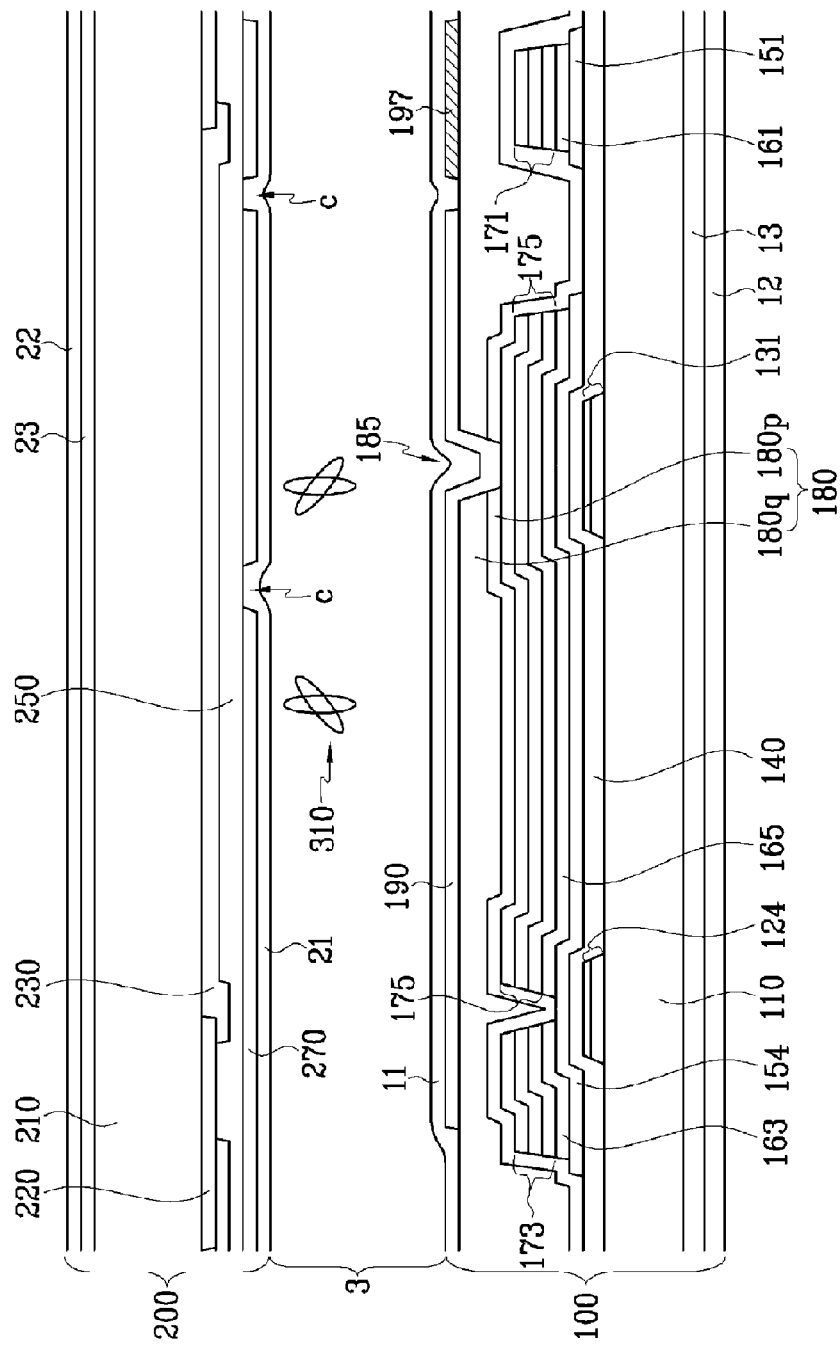

THIN FILM TRANSISTOR ARRAY PANEL AND LIQUID CRYSTAL DISPLAY INCLUDING LIGHT SHIELD

CROSS REFERENCE TO RELATED APPLICATION

This application claims priority to and the benefit of Korea Patent Application Nos. 10-2003-0068172 filed on Oct. 1, 2003, 10-2004-0011172 filed on Feb. 19, 2004, and 10-2004-0066755 filed on Aug. 24, 2004 in the Korean Intellectual Property Office, the entire content of which is incorporated herein by reference.

BACKGROUND OF THE INVENTION (a) Field of the Invention

The present invention relates to a thin film transistor array panel and a liquid crystal display including the same.

(b) Description of Related Art

A liquid crystal display (LCD) is one of the most widely used flat panel displays. LCDs are used in notebook or laptop computers, desktop computer monitors and televisions. LCDs are lightweight and occupy less space than conventional cathode ray tube (CRT) displays.

The general structure of an LCD consists of a liquid crystal (LC) layer that is positioned between pair of panels including field-generating electrodes such as pixel electrodes and a common electrode as well as polarizers. The LC layer is subject to an electric field generated by the electrodes and variations in the field strength change the molecular orientation of the LC layer and polarization of light passing through the LC layer. Appropriately positioned polarized filters block the polarized light, creating dark areas that can represent desired images.

One measure of LCD quality is aperture ratio. To increase aperture ratio, it has been suggested that the size of the pixel electrodes be maximized to be close to or to overlap data line for transmitting data voltages to the pixel electrodes. However, maximization of the size of the pixel electrodes results in a large parasitic capacitance between the pixel electrodes and the data lines, causing several defects. For example, the parasitic capacitance varies between exposure areas due to alignment deviations, which are divided in divisional exposure steps for forming the pixel electrodes and the data lines. The deviation of the parasitic capacitance yields deviation in transmittance between the exposure areas, causing stitch defect that boundaries of the exposure areas are caught.

SUMMARY OF THE INVENTION

A thin film transistor array panel is provided, which includes: a gate line; a data line intersecting the gate line; a thin film transistor connected to the gate line and the data line; a pixel electrode connected to the thin film transistor; a passivation layer formed on the data line; and a shielding electrode overlapping the data line at least in part and electrically disconnected from the data line.

The shielding electrode and the pixel electrode may be disposed on the passivation layer.

The passivation layer may include organic insulator such as a color filter.

The thin film transistor array panel may further include a storage electrode overlapping the pixel electrode. The storage electrode and the shielding electrode may be supplied with substantially the same voltage and in particular, they may be electrically connected to each other.

The shielding electrode may extend along the data line and fully cover the data line. The shielding electrode may include a pair of shielding stripes covering respective edges of the data line.

The shielding electrode may overlap the gate line at least in part. The shielding electrode may extend along the gate line and the data line and the shielding electrode is narrower than the gate line and wider than the data line.

The pixel electrode may have a chamfered edge, which may be equal to about four to ten microns.

The pixel electrode may have a cutout.

The data line may include may include an intersecting portion intersecting the gate line and a curved portion connected to the intersecting portion, and the pixel electrode may be curved along the curved portion of the data line.

A liquid crystal display is provided, which includes: a first panel including a gate line, a data line intersecting the gate line, a thin film transistor connected to the gate line and the data line, a pixel electrode connected to the thin film transistor, a passivation layer formed on the data line, and a shielding electrode overlapping the data line at least in part; and a second panel facing the first panel and including a common electrode formed thereon.

The common electrode and the shielding electrode may be supplied with substantially the same voltage, and in particular, they may be electrically connected to each other. The liquid crystal display may further include a storage electrode overlapping the pixel electrode and electrically connected to the common electrode.

The shielding electrode may be interposed between the common electrode and the data line.

The liquid crystal display may further include a liquid crystal layer that is disposed between the first panel and the second panel, has negative anisotropy, and is subjected to a vertical alignment.

The liquid crystal display may further include a tilt direction determining member for determining tilt directions of liquid crystal molecules in the liquid crystal layer. The tilt direction determining member may include a cutout of at least one of the pixel electrode and the common electrode or a protrusion disposed on at least one the pixel electrode and the common electrode.

The liquid crystal display may further include a pair of crossed polarizers disposed on the first and the second panels.

BRIEF DESCRIPTION OF THE DRAWINGS

The present invention will become more apparent by describing preferred embodiments thereof in detail with reference to the accompanying drawings in which:

FIG. 19A is a sectional view of the LCD shown in FIG. 18A taken along the line XIXA-XIXA';

DETAILED DESCRIPTION OF EMBODIMENTS

Figure 1:
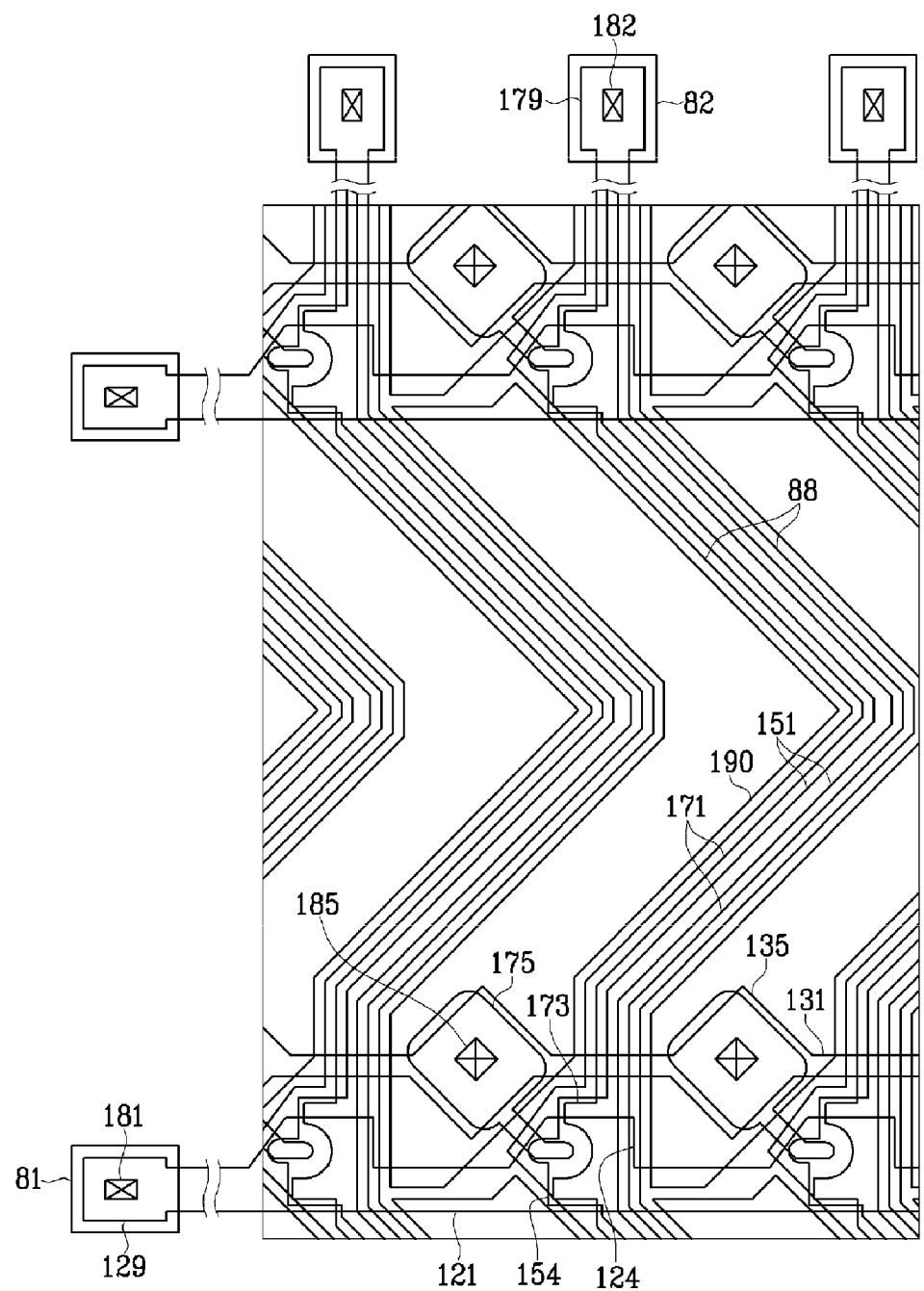
FIG. 1 is a layout view of a TFT array panel for an LCD according to an embodiment of the present invention.

The present invention now will be described more fully hereinafter with reference to the accompanying drawings, in which preferred embodiments of the invention are shown. The present invention may, however, be embodied in many different forms and should not be construed as limited to the embodiments set forth herein.

In the drawings, the thickness of layers, films and regions are exaggerated for clarity. Like numerals refer to like elements throughout. It will be understood that when an element such as a layer, film, region or substrate is referred to as being "on" another element, it can be directly on the other element or intervening elements may also be present. In contrast, when an element is referred to as being "directly on" another element, there are no intervening elements present.

Now, liquid crystal displays and thin film transistor (TFT) array panels for LCDs according to embodiments of the present invention will be described with reference to the accompanying drawings.

An LCD according to an embodiment of the present invention is described in detail with reference to FIGS. 1-5.

Figure 2:
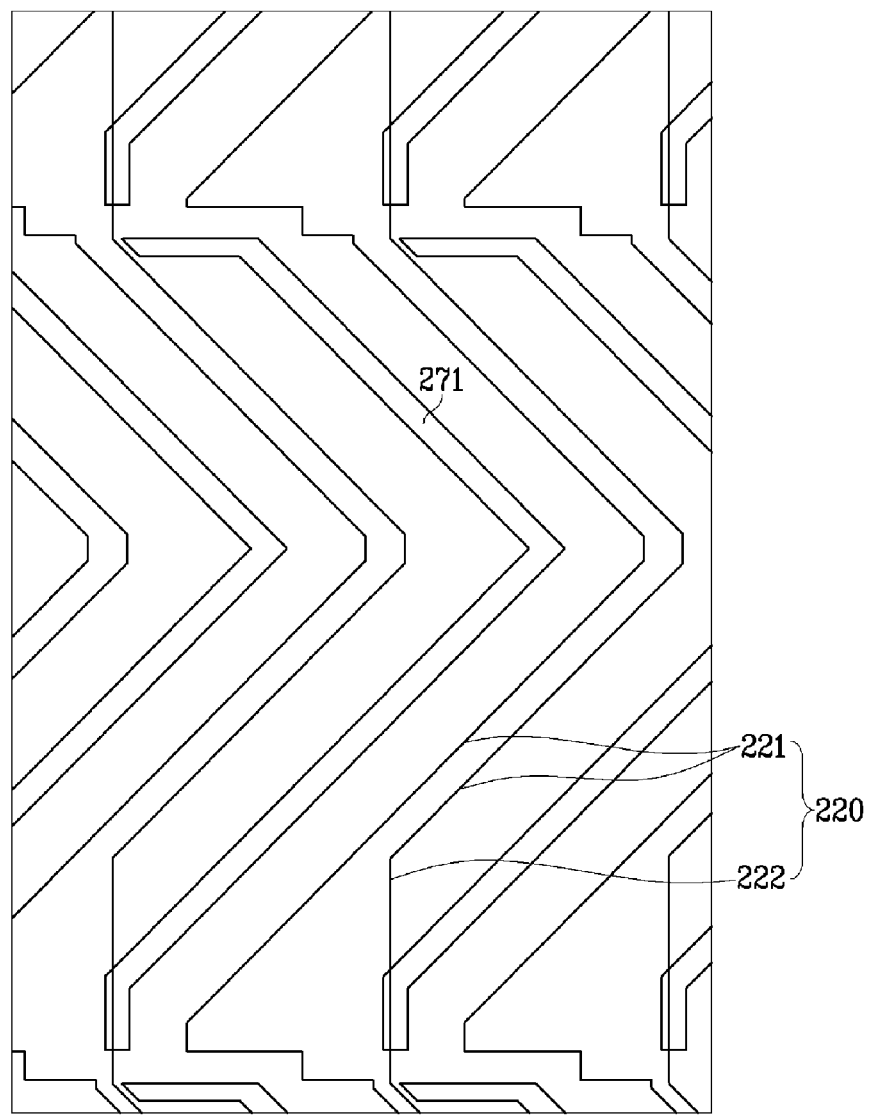
FIG. 2 is a layout view of a common electrode panel for an LCD according to an embodiment of the present invention.
Figure 3:
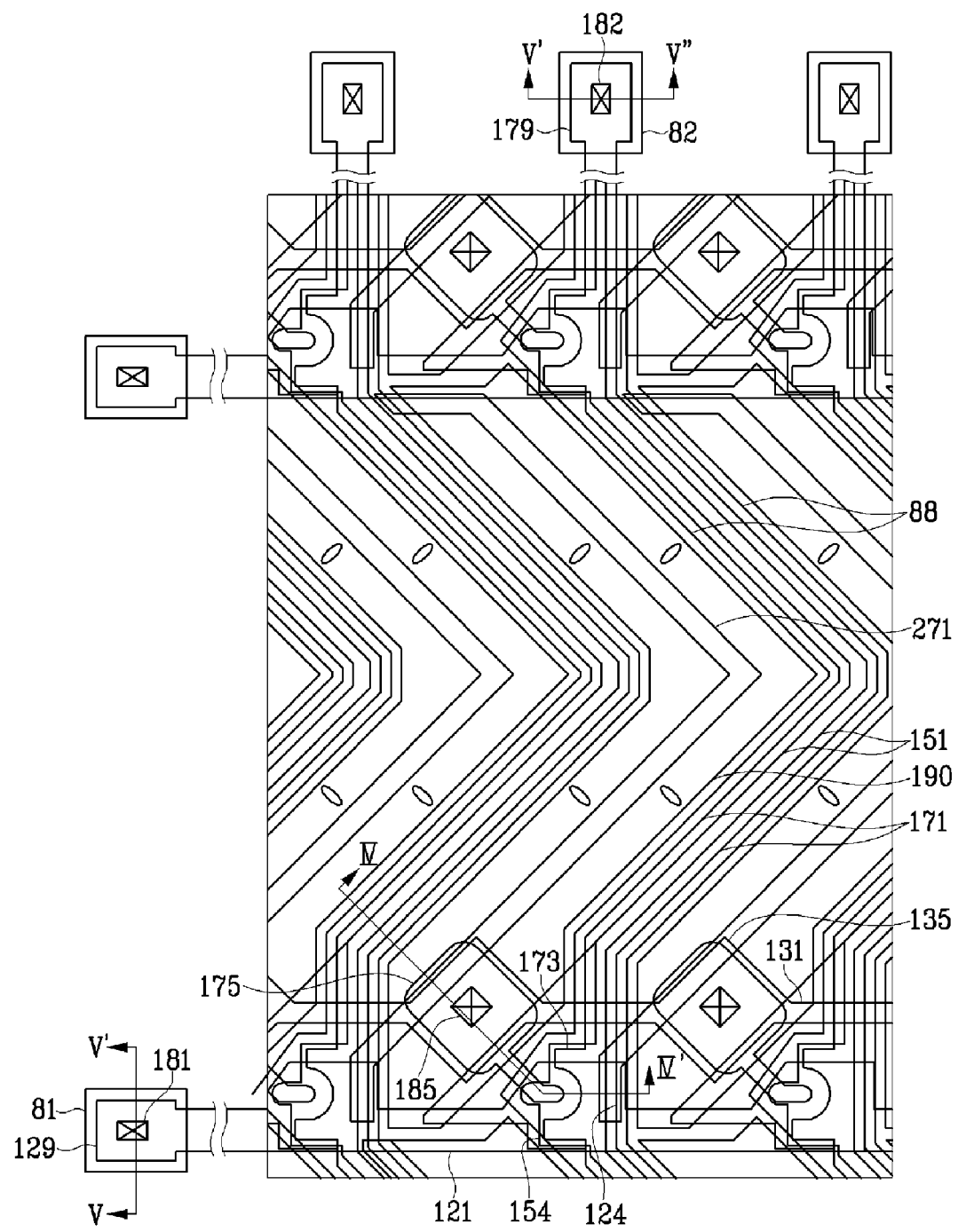
FIG. 3 is a layout view of an LCD including the TFT array panel shown in FIG. 1 and the common electrode panel shown in FIG. 2.
Figure 4:
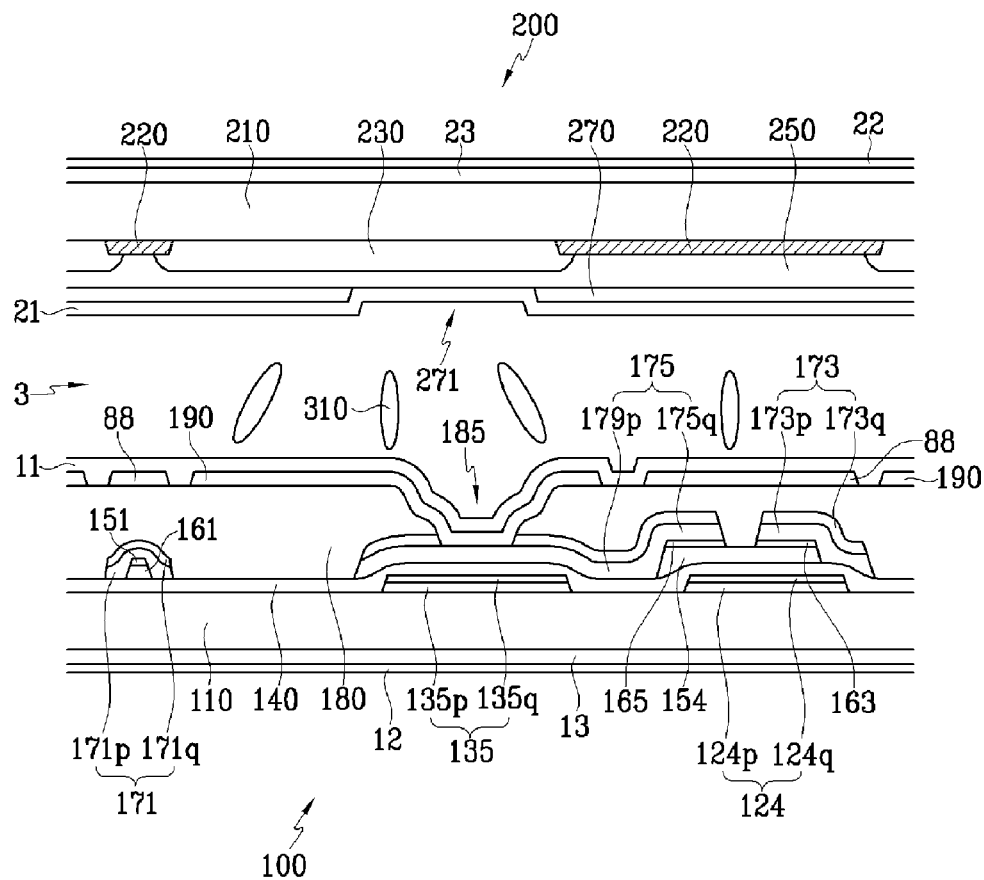
FIG. 4 is a sectional view of the LCD shown in FIG. 3 taken along the line IV-IV'.
Figure 5:
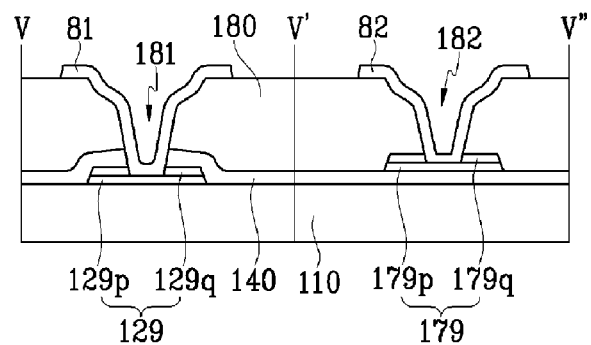
FIG. 5 is a sectional view of the LCD shown in FIG. 3 taken along the lines V-V' and V'-V''.

FIG. 1 is a layout view of a TFT array panel for an LCD according to an embodiment of the present invention, FIG. 2 is a layout view of a common electrode panel for an LCD according to an embodiment of the present invention, FIG. 3 is a layout view of an LCD including the TFT array panel shown in FIG. 1 and the common electrode panel shown in FIG. 2, FIG. 4 is a sectional view of the LCD shown in FIG. 3 taken along the line IV-IV', and FIG. 5 is a sectional view of the LCD shown in FIG. 3 taken along the lines V-V' and V'-V".

An LCD according to an embodiment of the present invention includes a TFT array panel 100, a common electrode panel 200 facing the TFT array panel 100, and a LC layer 3 interposed between the TFT array panel 100 and the common electrode panel 200.

The TFT array panel 100 is now described in detail with reference to FIGS. 1, 4 and 5.

A plurality of gate lines 121 and a plurality of storage electrode lines 131 are formed on an insulating substrate 110.

The gate lines 121 for transmitting gate signals extend substantially in a transverse direction and they are separated from each other. Each gate line 121 includes a plurality of projections forming a plurality of gate electrodes 124 and an end portion 129 having a large area for contact with another layer or an external device. The end portions 129 may not be provided when a gate driving circuit (not shown) is integrated on the substrate 110 such that the gate lines 121 in direct contact with the gate driving circuit.

Each storage electrode line 131 extends substantially in the transverse direction and includes a plurality of projections forming storage electrodes 135. Each storage electrode 135 has a shape of a diamond or a rectangle rotated by about 45 degrees and they are located close to the gate lines 121. The storage electrode lines 131 are supplied with a predetermined voltage such as a common voltage, which is applied to a common electrode 270 on the common electrode panel 200 of the LCD.

The gate lines 121 and the storage electrode lines 131 have a multi-layered structure including two films having different physical characteristics, a lower film and an upper film. The upper film is preferably made of low resistivity metal including Al containing metal such as Al and Al alloy, Ag containing metal such as Ag and Ag alloy, or Cu containing metal such as Cu and Cu alloy for reducing signal delay or voltage drop in the gate lines 121 and the storage electrode lines 131. On the other hand, the lower film is preferably made of material such as Cr, Mo, Mo alloy, Ta, or Ti, which has good physical, chemical, and electrical contact characteristics with other materials such as indium tin oxide (ITO) or indium zinc oxide (IZO). A good exemplary combination of the lower film material and the upper film material is Cr and Al—Nd alloy. In FIGS. 4 and 5, the lower and the upper films of the gate electrodes 124 are indicated by reference numerals 124p and 124q, respectively, the lower and the upper films of the end portions 129 are indicated by reference numerals 129p and 252, respectively, and the lower and the upper films of the storage electrodes 135 are indicated by reference numerals 135p and 135q, respectively. The upper film 252 of the end portions 129 of the gate lines 121 are removed at least in part to expose the lower films 129p.

The gate lines 121 and the storage electrode lines 131 may have a single layer structure or may include three or more layers.

In addition, the lateral sides of the gate lines 121 and the storage electrode lines 131 are inclined relative to a surface of the substrate 110, and the inclination angle thereof ranges about 30-80 degrees.

A gate insulating layer 140 preferably made of silicon nitride (SiNx) is formed on the gate lines 121 and the storage electrode lines 131.

A plurality of semiconductor stripes 151 preferably made of hydrogenated amorphous silicon (abbreviated as "a-Si") or polysilicon are formed on the gate insulating layer 140. Each semiconductor stripe 151 extends substantially in the longitudinal direction while it is curved periodically. Each semiconductor stripe 151 has a plurality of projections 154 branched out toward the gate electrodes 124.

A plurality of ohmic contact stripes and islands 161 and 165 preferably made of silicide or n+ hydrogenated a-Si heavily doped with n type impurity are formed on the semiconductor stripes 151. Each ohmic contact stripe 161 has a plurality of projections 163, and the projections 163 and the ohmic contact islands 165 are located in pairs on the projections 154 of the semiconductor stripes 151.

The lateral sides of the semiconductor stripes 151 and the ohmic contacts 161 and 165 are inclined relative to the surface of the substrate 110, and the inclination angles thereof are preferably in a range between about 30-80 degrees.

A plurality of data lines 171 and a plurality of drain electrodes 175 separated from each other are formed on the ohmic contacts 161 and 165 and the gate insulating layer 140.

The data lines 171 for transmitting data voltages extend substantially in the longitudinal direction and intersect the gate lines 121 and the storage electrode lines 131. Each data line 171 has an end portion 179 having a large area for contact with another layer or an external device and it includes a plurality of pairs of oblique portions and a plurality of longitudinal portions such that it curves periodically. A pair of oblique portions are connected to each other to form a chevron and opposite ends of the pair of oblique portions are connected to respective longitudinal portions. The oblique portions of the data lines 171 make an angle of about 45 degrees with the gate lines 121, and the longitudinal portions cross over the gate electrodes 124. The length of a pair of oblique portions is about one to nine times the length of a longitudinal portion, that is, it occupies about 50-90 percents of the total length of the pair of oblique portions and the longitudinal portion. A pair of oblique portions may be substituted with three or more oblique portions such that a part of a data line 171 between adjacent two longitudinal portions are curved twice or more.

Each drain electrode 175 includes a rectangular or rhombic expansion overlapping a storage electrode 135. The edges of the expansion of the drain electrode 175 are substantially parallel to the edges of the storage electrodes 135. Each longitudinal portion of the data lines 171 includes a plurality of projections such that the longitudinal portion including the projections forms a source electrode 173 partly enclosing an end portion of a drain electrode 175 disposed opposite the expansion. Each set of a gate electrode 124, a source electrode 173, and a drain electrode 175 along with a projection 154 of a semiconductor stripe 151 form a TFT having a channel formed in the semiconductor projection 154 disposed between the source electrode 173 and the drain electrode 175.

The data lines 171 and the drain electrodes 175 also include a lower film 171p and 175p preferably made of Mo, Mo alloy, Cr, Ta, or Ti and an upper film 171q and 175q located thereon and preferably made of Al containing metal, Ag containing metal, or Cu containing metal. In FIGS. 4 and 5, the lower and the upper films of the source electrodes 173 are indicated by reference numerals 173p and 173q, respectively, and the lower and the upper films of the end portions 179 of the data lines 171 are indicated by reference numerals 179p and 179q, respectively. The upper films 179q, 175q of the end portions 179 of the data lines 171 and the drain electrodes 175 are removed at least in part to expose the lower films 179p and 175p.

Like the gate lines 121 and the storage electrode lines 131, the data lines 171 and the drain electrodes 175 have inclined lateral sides, and the inclination angles thereof range about 30-80 degrees.

The ohmic contacts 161 and 165 are interposed only between the underlying semiconductor stripes 151 and the overlying data lines 171 and the overlying drain electrodes 175 thereon and reduce the contact resistance therebetween.

A passivation layer 180 is formed on the data lines 171 and the drain electrodes 175, and exposed portions of the semiconductor stripes 151, which are not covered with the data lines 171 and the drain electrodes 175. The passivation layer 180 is preferably made of photosensitive organic material having a good flatness characteristic, low dielectric insulating material such as a-Si:C:O and a-Si:O:F formed by plasma enhanced chemical vapor deposition (PECVD), or inorganic material such as silicon nitride and silicon oxide. The passivation layer 180 may have a double-layered structure including a lower inorganic film and an upper organic film in order to prevent the channel portions of the semiconductor stripes 151 from being in direct contact with organic material.

The passivation layer 180 has a plurality of contact holes 182 and 185 exposing the end portions 179 of the data lines 171 and the drain electrodes 175, respectively. The passivation layer 180 and the gate insulating layer 140 have a plurality of contact holes 181 exposing the end portions 129 of the gate lines 121. The above-described exposed portions of the lower films 129p, 179p and 175p are exposed through the contact holes 181, 182 and 185, respectively. The contact holes 181, 182 and 185 can have various shapes such as polygon or circle. The area of each contact hole 181 or 182 is preferably equal to or larger than 0.5 mm×15 μm and not larger than 2 mm×60 μm. The sidewalls of the contact holes 181, 182 and 185 are inclined with an angle of about 30-85 degrees or have stepwise profiles.

A plurality of pixel electrodes 190, a plurality of contact assistants 81 and 82, and a plurality of shielding electrodes 88, which are preferably made of transparent conductive material such as ITO or IZO, are formed on the passivation layer 180. For a reflective LCD, the pixel electrodes 190 may be made of opaque reflective material such as Ag or Al.

Each pixel electrode 190 is located substantially in an area enclosed by the data lines 171 and the gate lines 121, and thus it also forms a chevron. The pixel electrodes 190 cover the storage electrode lines 131 including the storage electrodes 135 and the expansions of the drain electrodes 175 and have chamfered edges substantially parallel to edges of the storage electrodes 135 that are close to the chamfered edges.

The pixel electrodes 190 are physically and electrically connected to the drain electrodes 175 through the contact holes 185 such that the pixel electrodes 190 receive the data voltages from the drain electrodes 175. The pixel electrodes 190 supplied with the data voltages generate electric fields in cooperation with the common electrode 270, which reorient liquid crystal molecules 310 disposed therebetween.

A pixel electrode 190 and the common electrode 270 form a capacitor called a "liquid crystal capacitor," which stores applied voltages after turn-off of the TFT. An additional capacitor called a "storage capacitor," which is connected in parallel to the liquid crystal capacitor, is provided for enhancing the voltage storing capacity. The storage capacitors are implemented by overlapping the pixel electrodes 190 with the storage electrode lines 131. The capacitances of the storage capacitors, i.e., the storage capacitances are increased by providing the projections (i.e., the storage electrodes) 135 at the storage electrode lines 131, elongating the drain electrodes 175 connected to the pixel electrodes 190, and providing the expansions at the drain electrodes 175 overlapping the storage electrodes 135 of the storage electrode lines 131 for decreasing the distance between the terminals and increasing the overlapping areas.

The pixel electrodes 190 overlap the data lines 171 as well as the gate lines 121 to increase aperture ratio.

The contact assistants 81 and 82 are connected to the exposed end portions 129 of the gate lines 121 and the exposed end portions 179 of the data lines 171 through the contact holes 181 and 182, respectively. The contact assistants 81 and 82 protect the exposed portions 129 and 179 and complement the adhesion between the exposed portions 129 and 179 and external devices. The contact assistants 81 and 82 are connected to external devices through anisotropic conductive films (ACF) (not shown), etc.

The contact assistants 81 may play a role connecting the gate lines 121 and metal layers of a gate driving circuit, if it is integrated on the TFT array panel. Similarly, the contact assistants 82 may play a role connecting the data lines 171 and metal layers of a data driving circuit, if it is integrated on the TFT array panel.

The shielding electrodes 88 extend along the data lines 171 and fully cover the data lines 171 and the TFTs. However, the shielding electrodes 88 may be narrower than the data lines 171. The shielding electrodes 88 are supplied with the common voltage and they may be connected to the storage electrode lines 131 through contact holes (not shown) penetrating the gate insulating layer 140 and the passivation layer 180 or connected to short points (not shown) where the common voltage is transmitted from the TFT array panel 100 to the common electrode panel 200. The distance between the shielding electrodes 88 and the pixel electrodes 190 is preferably minimized to minimize the decrease of the aperture ratio.

The shielding electrodes 88 supplied with the common voltage can block electric fields generated between the pixel electrodes 190 and the data lines 171 and between the common electrode 270 and the data lines 171 such that the distortion of the voltage of the pixel electrodes 190 and the signal delay of the data voltages transmitted by the data lines 171 are reduced.

Furthermore, since the pixel electrodes 190 are required to be spaced apart from the shielding electrodes 88 for preventing the short therebetween, the pixel electrodes 190 become farther from the data lines 171 such that the parasitic capacitance therebetween becomes reduced. Moreover, since the permittivity of the LC layer 3 is larger than that of the passivation layer 180, the parasitic capacitance between the data lines 171 and the shielding electrodes 88 is reduced compared with that between the data lines 171 and the common electrode 270 without the shielding electrodes 88. Simulations showed that the parasitic capacitance between the pixel electrodes 190 and the data lines 171 with the shielding electrodes 88 is smaller than about one tenth of that without the shielding electrodes 88 and the parasitic capacitance between the data lines 171 and the shielding electrodes 88 is about 70-80% of the parasitic capacitance between the data lines 171 and the common electrode 270 without the shielding electrodes 88.

In addition, the distance between the pixel electrodes 190 and the shielding electrodes 88 can be uniformly maintained since they are made of the same layer and thus the parasitic capacitance therebetween can be made uniform. Although the parasitic capacitance between the pixel electrodes 190 and the data lines 171 may be still varied between exposure areas divided in a divisional exposure process, the total parasitic capacitance can be nearly uniform since the parasitic capacitance between the pixel electrodes 190 and the data lines 171 is relatively reduced. Accordingly, the stitch defect is reduced.

Finally, a homeotropic alignment layer 11 is formed on the pixel electrodes 190, the contact assistants 81 and 82, and the passivation layer 180.

The description of the common electrode panel 200 follows with reference to FIGS. 2, 4 and 5.

A light blocking member called a black matrix 220 is formed on an insulating substrate 210 such as transparent glass and it includes a plurality of oblique portions 221 facing the oblique portions of the data lines 171 and a plurality of right-angled-triangular portions 222 facing the TFTs and the longitudinal portions of the data lines 171 such that the light blocking member 220 prevents light leakage between the pixel electrodes 190 and defines open areas facing the pixel electrodes 190. Each of the triangular portions of the light blocking member 220 has a hypotenuse parallel to a chamfered edge of a pixel electrode 190.

A plurality of color filters 230 are formed on the substrate 210 and the light blocking member 220 and it is disposed substantially in the open areas defined by the light blocking member 220. The color filters 230 disposed in adjacent two data lines 171 and arranged in the longitudinal direction may be connected to each other to form a stripe. Each color filter 230 may represent one of three primary colors such as red, green and blue colors.

An overcoat 250 preferably made of organic material is formed on the color filters 230 and the light blocking member 220. The overcoat 250 protects the color filters 230 and has a flat top surface.

A common electrode 270 preferably made of transparent conductive material such as ITO and IZO is formed on the overcoat 250. The common electrode 270 is supplied with the common voltage and it has a plurality of chevron-like cutouts 271. Each cutout 271 includes a pair of oblique portions connected to each other, a transverse portion connected to one of the oblique portions, and a longitudinal portion connected to the other of the oblique portions. The oblique portions of the cutout 271 extend substantially parallel to the oblique portions of the data lines 171 and face a pixel electrode 190 so that they may bisect the pixel electrode 190 into left and right halves. The transverse and the longitudinal portions of the cutout 271 are aligned with transverse and longitudinal edges of the pixel electrode 190, respectively, and they make obtuse angles with the oblique portions of the cutout 271. The cutouts 271 are provided for controlling the tilt directions of the LC molecules 310 in the LC layer 3 and preferably have a width in a range between about 9-12 microns. The cutouts 271 may be substituted with protrusions formed on or under the common electrode 270, preferably made of organic material, and preferably having width ranging about 5 microns to 10 microns.

A homeotropic alignment layer 21 is coated on the common electrode 270.

A pair of polarizers 12 and 22 are provided on outer surfaces of the panels 100 and 200 such that their transmissive axes are crossed and one of the transmissive axes, for example, the transmissive axis of the polarizer 12 provided on the TFT array panel 100 is parallel to the gate lines 121. The polarizer 12 may be omitted for a reflective LCD.

The LCD further includes retardation films 13 and 23 interposed between the panels 100 and 200 and the polarizers 12 and 22. The retardation films 13 and 23 have birefringence and compensate the retardation of the LC layer 3 in a reversed manner. The retardation films 13 and 23 may include uniaxial or biaxial optical films, and in particular, they may include negative uniaxial optical films.

The LCD may further include a backlight unit for providing light for the polarizers 12 and 22, the panels 100 and 200, and the LC layer 3.

The alignment layers 11 and 21 may be homogeneous alignment layers.

The LC layer 3 has negative dielectric anisotropy and the LC molecules 310 in the LC layer 3 are aligned such that their long axes are vertical to the surfaces of the panels in absence of electric field. Accordingly, incident light cannot pass the crossed polarization system 12 and 22.

Upon application of the common voltage to the common electrode 270 and a data voltage to the pixel electrodes 190, a primary electric field substantially perpendicular to the surfaces of the panels is generated. The LC molecules 310 tend to change their orientations in response to the electric field such that their long axes are perpendicular to the field direction. In the meantime, the cutouts 271 of the common electrode 270 and the edges of the pixel electrodes 190 distort the primary electric field to have a horizontal component which determines the tilt directions of the LC molecules 310. The horizontal component of the primary electric field is perpendicular to the edges of the cutouts 271 and the edges of the pixel electrodes 190. The horizontal components of the primary electric field at opposite edges of a cutout are antiparallel.

Accordingly, four sub-regions having different tilt directions, which are partitioned by edges of a pixel electrode 190, a cutout 271 bisecting the pixel electrode 190, and an imaginary transverse center line passing through the meeting point of the oblique portions of the cutout 271, are formed in a pixel region of the LC layer 3, which are located on the pixel electrode 190. Each sub-region has two major edges defined by the cutout 271 and an oblique edge of the pixel electrode 190, respectively, which are spaced apart preferably from about 10 microns to about 30 microns. The number of the sub-regions in a pixel region is preferably four if the planar area of the pixel region is smaller than about 100×300 square microns, and, if not, it is preferably four or eight. The number of the sub-regions can be varied by changing the number of the cutouts 271 of the common electrode 270, by providing cutouts at the pixel electrodes 190, or by changing the number of curved points of the edges of the pixel electrodes 190. The sub-regions are classified into a plurality of, preferably four, domains based on the tilt directions.

In the meantime, the direction of a secondary electric field due to the voltage difference between the pixel electrodes 190 is perpendicular to the edges of the cutouts 271. Accordingly, the field direction of the secondary electric field coincides with that of the horizontal component of the primary electric field. Consequently, the secondary electric field between the pixel electrodes 190 enhances the determination of the tilt directions of the LC molecules 310.

Since the LCD performs inversion such as dot inversion, column inversion, etc., adjacent pixel electrodes are supplied with data voltages having opposite polarity with respect to the common voltage and thus a secondary electric field between the adjacent pixel electrodes 190 is almost always generated to enhance the stability of the domains.

In the meantime, the magnitude of the electric field between the common electrode 270 and the shielding electrodes 88 is nearly zero since the common electrode 270 and the shielding electrodes 88 are supplied with the same voltage, i.e., the common voltage. Therefore, the LC molecules 310 disposed between the common electrode 270 and the shielding electrodes 88 maintains their initially vertical alignments such that light incident on those regions may be blocked rather than transmitted.

Since the tilt directions of all domains make an angle of about 45 degrees with the gate lines 121, which are parallel to or perpendicular to the edges of the panels 100 and 200, and the 45-degree intersection of the tilt directions and the transmissive axes of the polarizers 12 and 22 gives maximum transmittance, the polarizers 12 and 22 can be attached such that the transmissive axes of the polarizers 12 and 22 are parallel to or perpendicular to the edges of the panels 100 and 200 and it reduces the production cost.

The resistance increase of the data lines 171 due to the curving can be compensated by widening the data lines 171 since distortion of the electric field and increase of the parasitic capacitance due to the increase of the width of the data lines 171 can be compensated by maximizing the size of the pixel electrodes 190 and by adapting a thick organic passivation layer.

A method of manufacturing the TFT array panel shown in FIGS. 1-5 according to an embodiment of the present invention will be now described in detail.

A lower conductive film preferably made of Cr, Mo, or Mo alloy and an upper conductive film preferably made of Al containing metal or Ag containing metal are sputtered in sequence on an insulating substrate 110 and they are wet or dry etched in sequence to form a plurality of gate lines 121, each including a plurality of gate electrodes 124 and an end portion 129, and a plurality of storage electrode lines 131 including a plurality of storage electrodes 135.

After sequential deposition of a gate insulating layer 140 with thickness of about 1,500-5,000 Å, an intrinsic a-Si layer with thickness of about 500-2,000 Å, and an extrinsic a-Si layer with thickness of about 300-600 Å, the extrinsic a-Si layer and the intrinsic a-Si layer are photo-etched to form a plurality of extrinsic semiconductor stripes and a plurality of intrinsic semiconductor stripes 151 including a plurality of projections 154 on the gate insulating layer 140.

Subsequently, two conductive films including a lower conductive film and an upper conductive film and having a thickness of 1,500-3,000 Å are sputtered in sequence and patterned to form a plurality of date lines 171, each including a plurality of source electrodes 173 and an end portion 179, and a plurality of drain electrodes 175. The lower conductive film is preferably made of Cr, Mo, or Mo alloy, and the upper conductive film is preferably made of Al containing metal or Ag containing metal.

Thereafter, portions of the extrinsic semiconductor stripes, which are not covered with the data lines 171 and the drain electrodes 175, are removed to complete a plurality of ohmic contact stripes 161 including a plurality of projections 163 and a plurality of ohmic contact islands 165 and to expose portions of the intrinsic semiconductor stripes 151. Oxygen plasma treatment preferably follows in order to stabilize the exposed surfaces of the semiconductor stripes 151.

A passivation layer 180 made of a positive photosensitive organic insulator is coated and exposed through a photo-mask (not shown) having transmissive areas (not shown), slit areas (not shown) disposed around the transmissive areas, and light blocking areas. Accordingly, portions of the passivation layer 180 facing the transmissive areas absorb the full energy of the light, while portions of the passivation layer 180 facing the slit areas partially absorb the light energy. The passivation layer 180 is then developed to form a plurality of contact holes 182 and 185 exposing portions of the end portions 179 of the data lines 171 and portions of the drain electrodes 175, respectively, and to form upper portions of a plurality of contact holes 181 exposing portions of the gate insulating layer 140 disposed on the end portions 129 of the gate lines 121. Since the portions of the passivation layer 180 facing the transmissive areas are removed to its full thickness, while the portions facing the slit areas remain to have reduced thickness, sidewalls of the contact holes 181, 182 and 185 have stepped profiles.

The passivation layer 180 may be made of negative photosensitive material and, in this case, the light blocking areas and the transmissive areas are exchanged in comparison with the positive photosensitive material.

After removing the exposed portions of the gate insulating layer 140 to expose the underlying portions of the end portions 129 of the gate lines 121, the exposed portions of the upper conductive films $175q$, $179q$ and $129q$ of the drain electrodes 175, the end portions 179 of the data lines 171, and the end portions 129 of the gate lines 121 are removed to expose underlying portions of the lower conductive films $175p$, $179p$ and $129p$ of the drain electrodes 175, the end portions 179 of the data lines 171, and the end portions 129 of the gate lines 121.

Finally, a plurality of pixel electrodes 190, a plurality of shielding electrodes 88, and a plurality of contact assistants 81 and 82 are formed on the passivation layer 180 and on the exposed portions of the lower conductive films $175p$, $179p$ and $129p$ of the drain electrodes 175, the end portions 129 of the gate lines 121, and the end portions 179 of the data lines 171 by sputtering and photo-etching an IZO or ITO layer with thickness of about 400-500 Å as shown in FIGS. 1, 4 and 5.

An LCD according to another embodiment of the present invention will be described in detail with reference to FIGS. 6-8.

Figure 6:
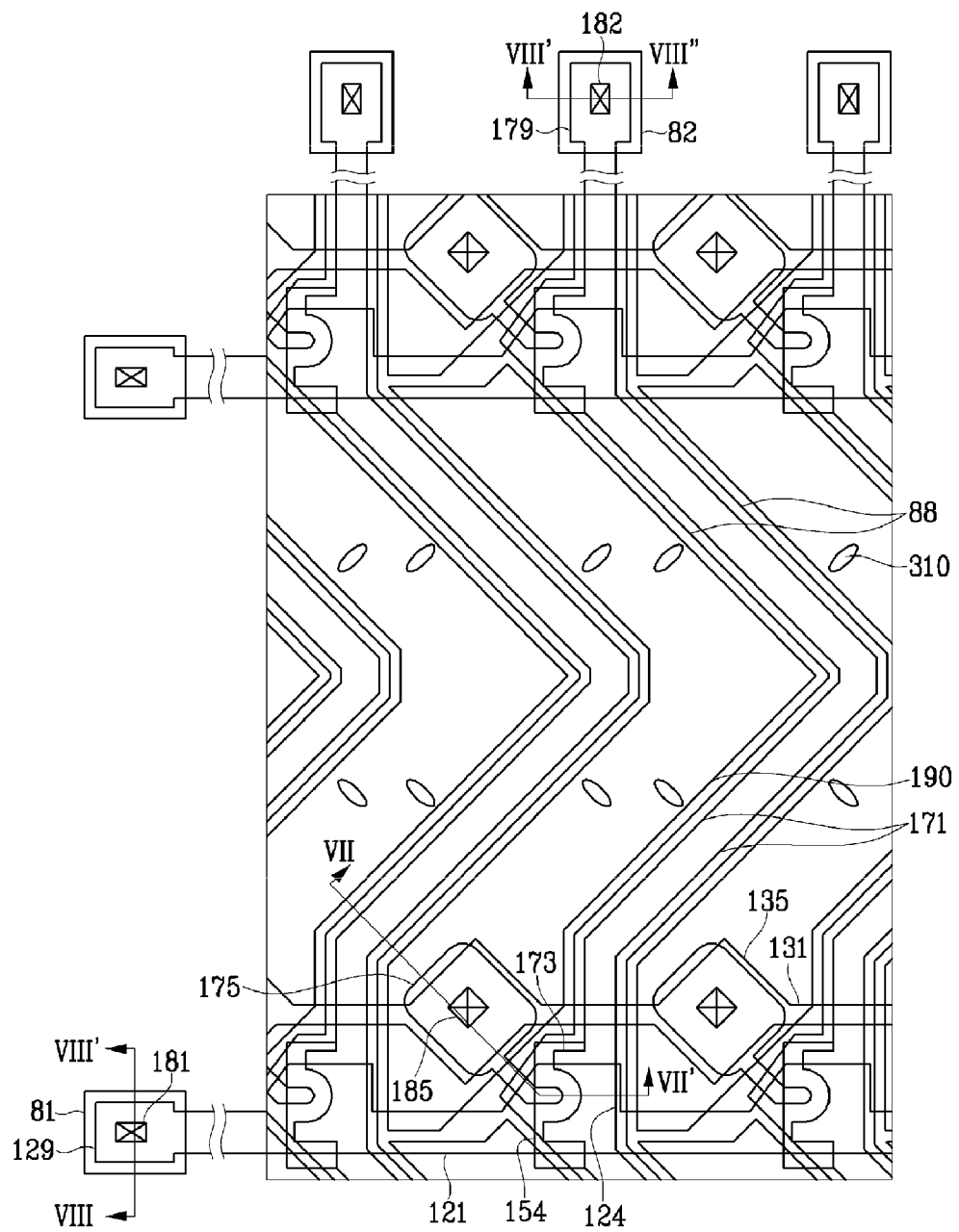
FIG. 6 is a layout view of an LCD according to another embodiment of the present invention.
Figure 7:
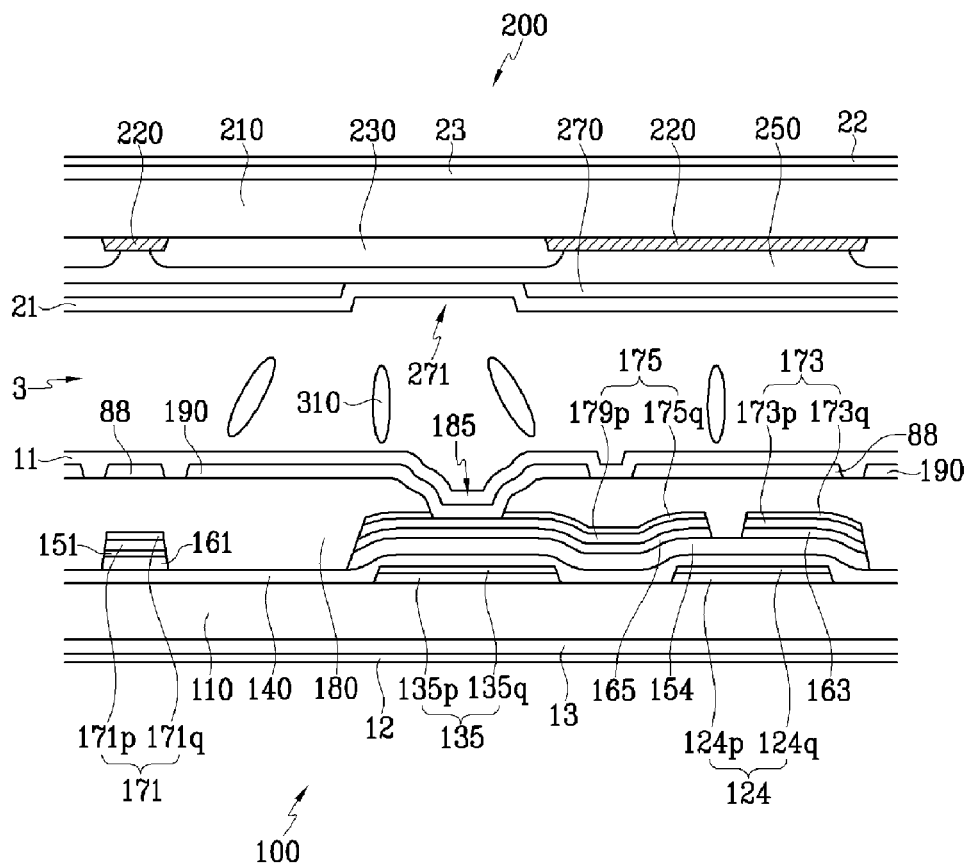
FIG. 7 is a sectional view of the LCD shown in FIG. 6 taken along the line VII-VII'.
Figure 8:
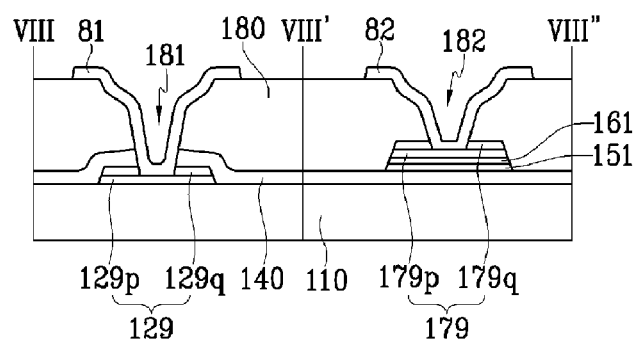
FIG. 8 is a sectional view of the LCD shown in FIG. 6 taken along the lines VIII-VIII' and VIII'-VIII''.

FIG. 6 is a layout view of an LCD according to another embodiment of the present invention, FIG. 7 is a sectional view of the LCD shown in FIG. 6 taken along the line VII-VII', and FIG. 8 is a sectional view of the LCD shown in FIG. 6 taken along the lines VIII-VIII' and VIII'-VIII".

Referring to FIGS. 6-8, an LCD according to this embodiment also includes a TFT array panel 100, a common electrode panel 200, a LC layer 3 interposed therebetween, a pair of retardation films 13 and 23 attached to outer surfaces of the panels 100 and 200, and a pair of polarizers 11 and 21 attached to outer surfaces of the retardation films 13 and 23.

Layered structures of the panels 100 and 200 according to this embodiment are almost the same as those shown in FIGS. 1-5.

Regarding the TFT array panel 100, a plurality of gate lines 121 including a plurality of gate electrodes 124 and a plurality of storage electrode lines 131 including a plurality of storage electrodes 135 are formed on a substrate 110, and a gate insulating layer 140, a plurality of semiconductor stripes 151 including a plurality of projections 154, and a plurality of ohmic contact stripes 161 including a plurality of projections 163 and a plurality of ohmic contact islands 165 are sequentially formed thereon. A plurality of data lines 171 including a plurality of source electrodes 173 and a plurality of drain electrodes 175 are formed on the ohmic contacts 161 and 165, and a passivation layer 180 is formed thereon. A plurality of contact holes 181, 182 and 185 are provided at the passivation layer 180 and the gate insulating layer 140. A plurality of pixel electrodes 190, a plurality of shielding electrodes 88, and a plurality of contact assistants 81 and 82 are formed on the passivation layer 180, and an alignment layer 11 is coated thereon.

Regarding the common electrode panel 200, a light blocking member 220, a plurality of color filters 230, an overcoat 250, a common electrode 270, and an alignment layer 21 are formed on an insulating substrate 210.

Different from the LCD shown in FIGS. 1-5, the semiconductor stripes 151 have almost the same planar shapes as the data lines 171 and the drain electrodes 175 as well as the underlying ohmic contacts 161 and 165. However, the projections 154 of the semiconductor stripes 151 include some exposed portions, which are not covered with the data lines 171 and the drain electrodes 175, such as portions located between the source electrodes 173 and the drain electrodes 175.

A manufacturing method of the TFT array panel according to an embodiment simultaneously forms the data lines 171, the drain electrodes 175, the semiconductors 151, and the ohmic contacts 161 and 165 using one photolithography process.

A photoresist pattern for the photolithography process has position-dependent thickness, and in particular, it has first and second portions with decreased thickness. The first portions are located on wire areas that will be occupied by the data lines 171 and the drain electrodes 175 and the second portions are located on channel areas of TFTs.

The position-dependent thickness of the photoresist is obtained by several techniques, for example, by providing translucent areas on the exposure mask as well as transparent areas and light blocking opaque areas. The translucent areas may have a slit pattern, a lattice pattern, a thin film(s) with intermediate transmittance or intermediate thickness. When using a slit pattern, it is preferable that the width of the slits or the distance between the slits is smaller than the resolution of a light exposer used for the photolithography. Another example is to use reflowable photoresist. In detail, once a photoresist pattern made of a reflowable material is formed by using a normal exposure mask only with transparent areas and opaque areas, it is subject to reflow process to flow onto areas without the photoresist, thereby forming thin portions.

As a result, the manufacturing process is simplified by omitting a photolithography step.

Many of the above-described features of the LCD shown in FIGS. 1-5 may be appropriate to the LCD shown in FIGS. 6-8.

An LCD according to another embodiment of the present invention will be described in detail with reference to FIGS. 9 and 10.

Figure 9:
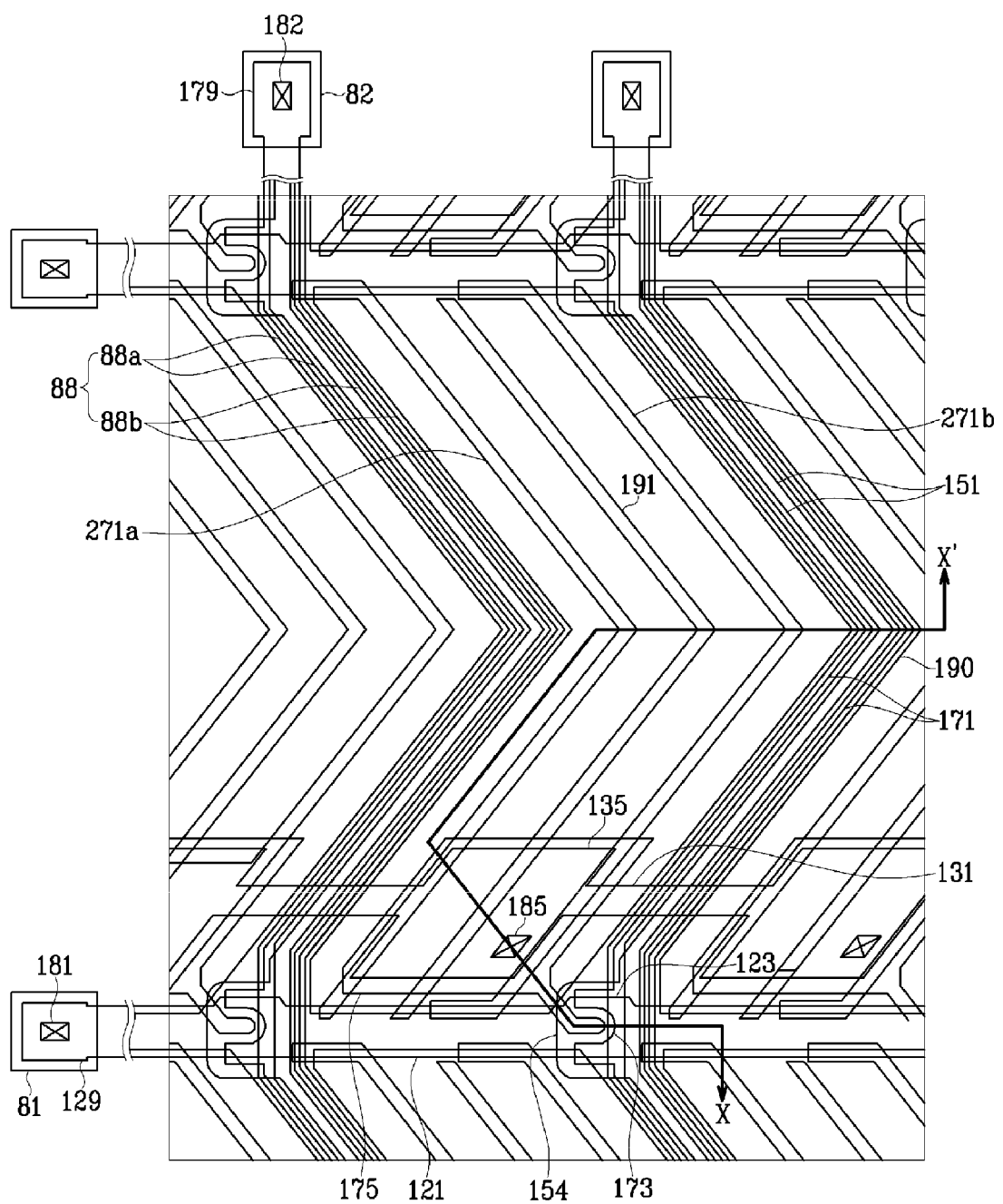
FIG. 9 is a layout view of an LCD according to another embodiment of the present invention.
Figure 10:
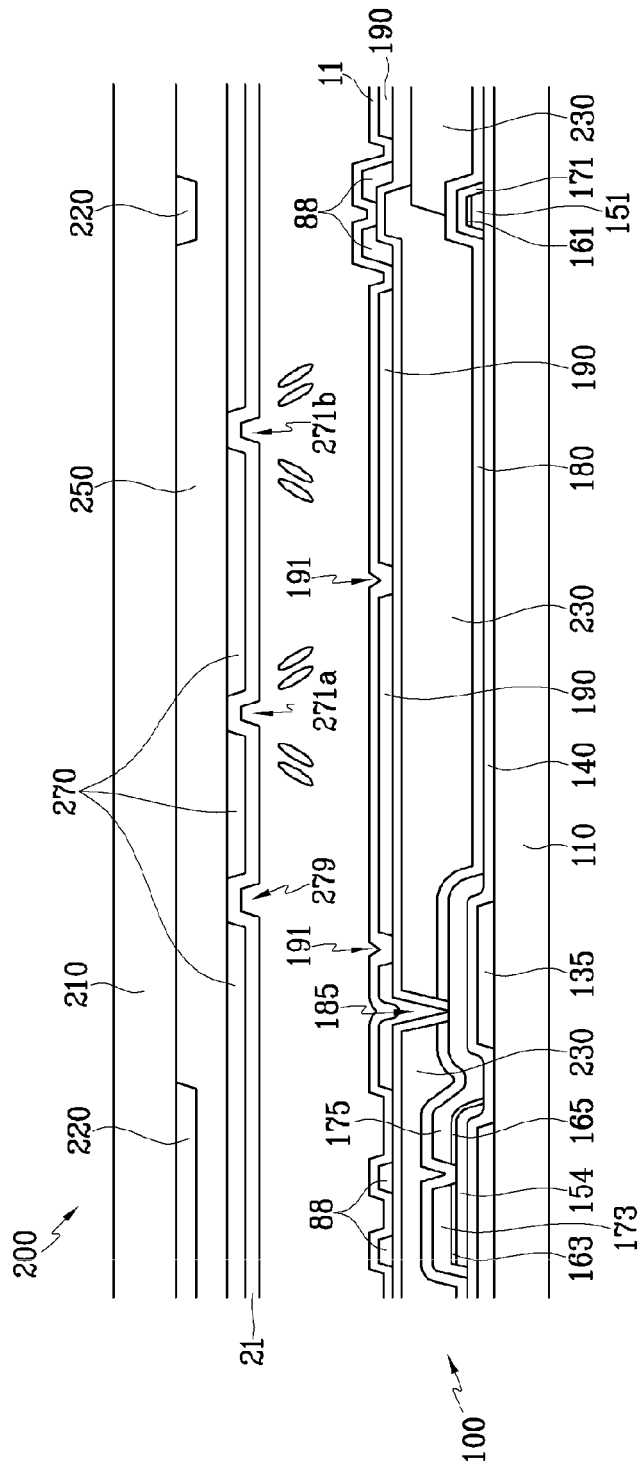
FIG. 10 is a sectional view of the LCD shown in FIG. 9 taken along the lines X-X'.

FIG. 9 is a layout view of an LCD according to another embodiment of the present invention, and FIG. 10 is a sectional view of the LCD shown in FIG. 9 taken along the lines X-X'.

Referring to FIGS. 9 and 10, an LCD according to this embodiment also includes a TFT array panel 100, a common electrode panel 200, and a LC layer 3 interposed therebetween.

Layered structures of the panels 100 and 200 according to this embodiment are almost the same as those shown in FIGS. 1-5.

Regarding the TFT array panel 100, a plurality of gate lines 121 including a plurality of gate electrodes 124 and a plurality of storage electrode lines 131 including a plurality of storage electrodes 135 are formed on a substrate 110, and a gate insulating layer 140, a plurality of semiconductor stripes 151 including a plurality of projections 154, and a plurality of ohmic contact stripes 161 including a plurality of projections 163 and a plurality of ohmic contact islands 165 are sequentially formed thereon. A plurality of data lines 171 including a plurality of source electrodes 173 and a plurality of drain electrodes 175 are formed on the ohmic contacts 161 and 165, and a passivation layer 180 is formed thereon. A plurality of contact holes 181, 182 and 185 are provided at the passivation layer 180 and the gate insulating layer 140. A plurality of pixel electrodes 190, a plurality of shielding electrodes 88, and a plurality of contact assistants 81 and 82 are formed on the passivation layer 180, and an alignment layer 11 is coated thereon.

Regarding the common electrode panel 200, a light blocking member 220, an overcoat 250, a common electrode 270, and an alignment layer 21 are formed on an insulating substrate 210.

Different from the LCD shown in FIGS. 1-5, each shielding electrode 88 includes a pair of shielding stripes 88a and 88b that overlap respective edges of a data line 171.

In addition, each pixel electrode 190 has a cutout 191. Each cutout 191 includes a pair of oblique portions that extending parallel to the data lines 171 and bisects the pixel electrode 190 into left and right partitions. Related to the cutout 191 of the pixel electrode 190, the common electrode 270 has a plurality of pairs of cutouts 271a and 271b parallel to the cutouts 191 and bisecting the partitions of the pixel electrodes 190 into left and right portions.

Although the figures show that a pair of partitions forming a pixel electrode 190 are interposed between adjacent data lines 171, the partitions may be separated by a data line 171.

Furthermore, the storage electrodes 135, the expansions of the drain electrodes 175, and the contact holes 185 exposing portions of the drain electrodes 175 have shapes of parallelogram.

Moreover, a plurality of color filters 230 are provided on the passivation layer 180, while there is no color filter on the common electrode panel 200. The overcoat 250 can be also omitted. Each of the color filters 230 represent one of primary colors such as red, green and blue and it may be disposed substantially between adjacent two the data lines 171. The color filters 230 between adjacent two data lines 171 and arranged in the longitudinal direction may be connected to each other to form a periodically-curved stripe. The color filters 230 have a plurality of openings on the contact holes 185 exposing the drain electrodes 175. The color filters 230 are not disposed on a peripheral area which is provided with expanded end portions 129 and 179 of the gate lines 121 and the data lines 171. The color filters 230 overlap each other on the data lines 171 to block the light leakage between the pixel electrodes 190 and portions of the light blocking member 220 around the pixel electrodes 190 may be omitted. The edges of the color filters 230 may be covered with the shielding electrodes 88. The overlapping portions of the color filters 230 may be thinner than other portions and the thickness variation of the color filters 230 may be obtained by using a photo-mask having slit areas or translucent areas for forming the color filters 230 and aligning the slit areas or the translucent areas with the overlapping portions. However, adjacent color filters 230 may be spaced apart from each other or the edges thereof may exactly match each other.

Each of the gate lines 121, the storage electrode lines 131, the data lines 171, and the drain electrodes 175 include a single film that may be made of Al containing metal, Ag containing metal, Cu containing metal, Mo containing metal, Cr, Ti or Ta. In particular, the data lines 171 and the drain electrodes 175 may be made of refractory metal such as Cr, Mo, Ta and Ti or alloys thereof.

Many of the above-described features of the LCD shown in FIGS. 1-5 may be appropriate to the LCD shown in FIGS. 9 and 10.

An LCD according to another embodiment of the present invention will be described in detail with reference to FIGS. 11-14.

Figure 11:
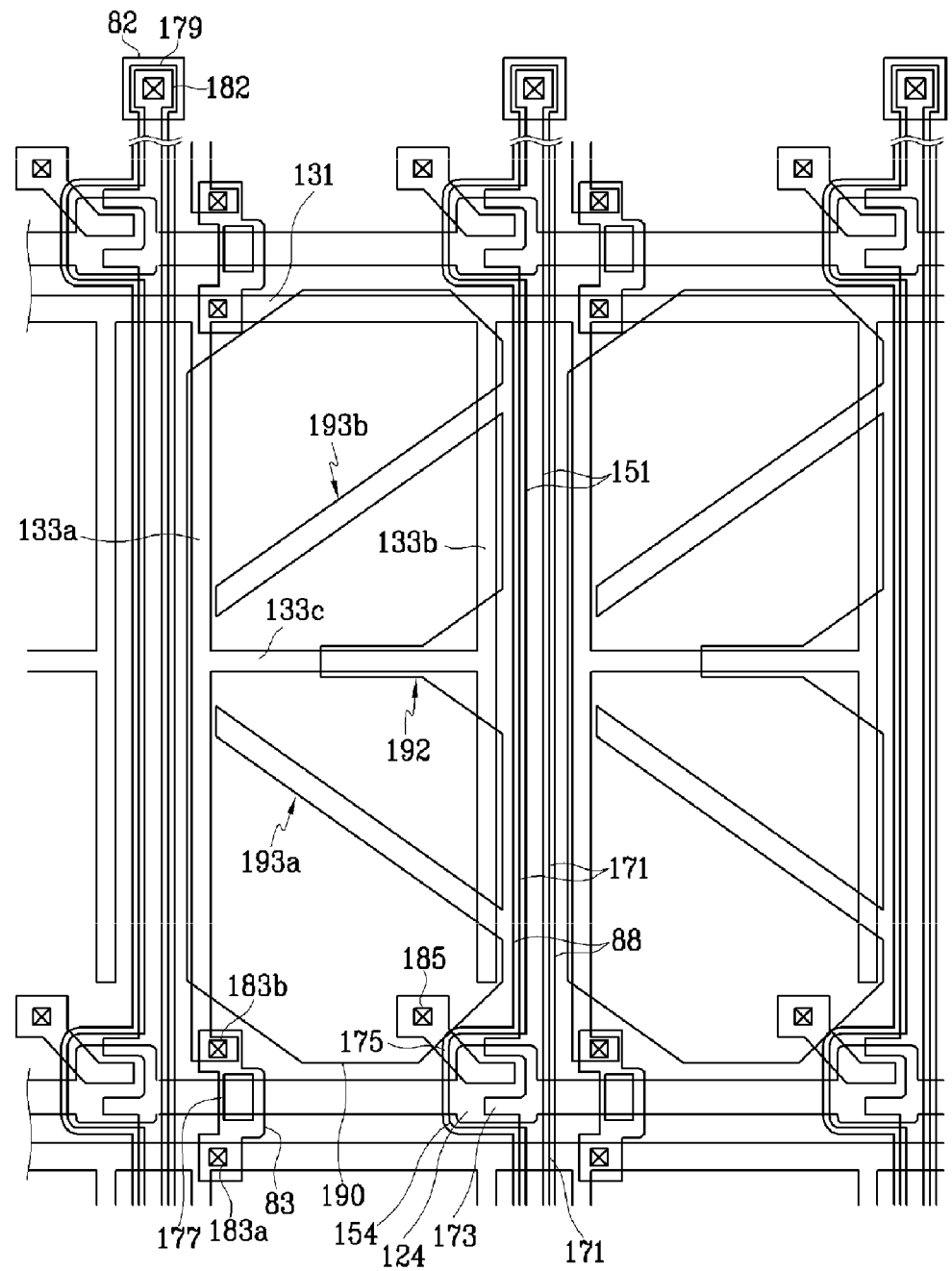
FIG. 11 is a layout view of a TFT array panel of an LCD according to another embodiment of the present invention.
Figure 12:
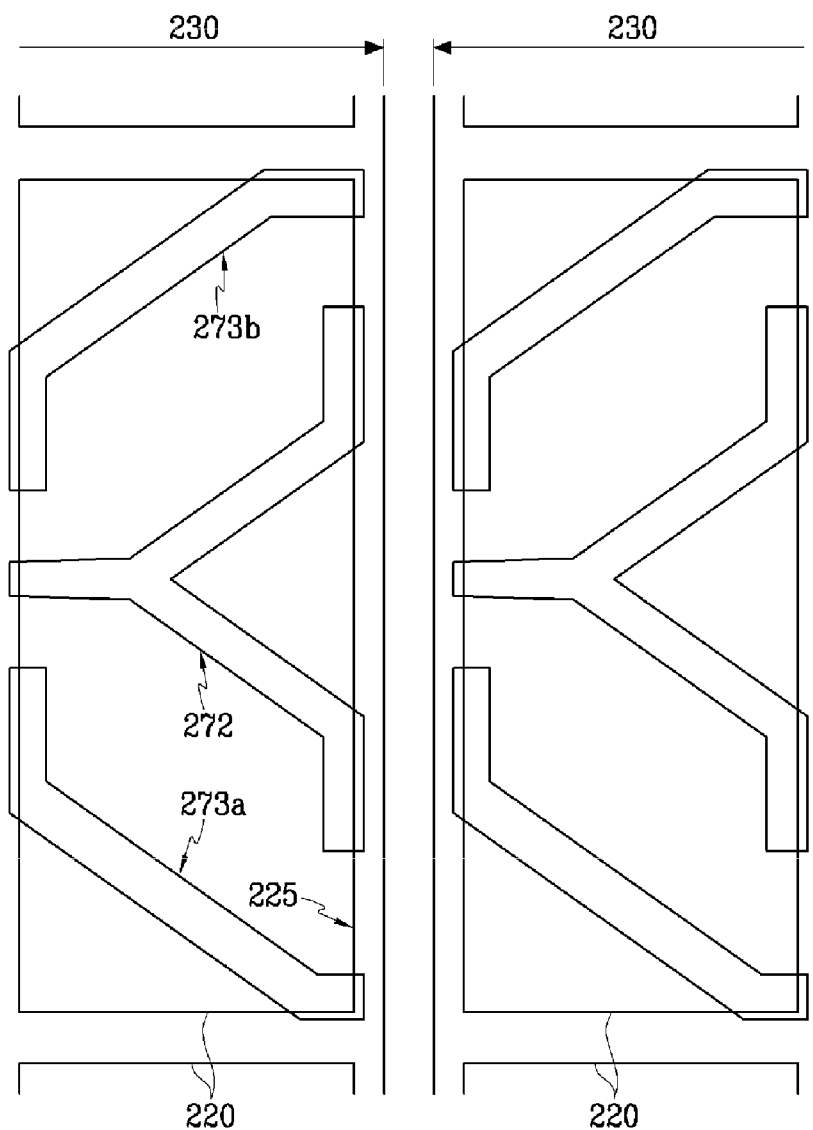
FIG. 12 is a layout view of a common electrode panel of an LCD according to another embodiment of the present invention.
Figure 13:
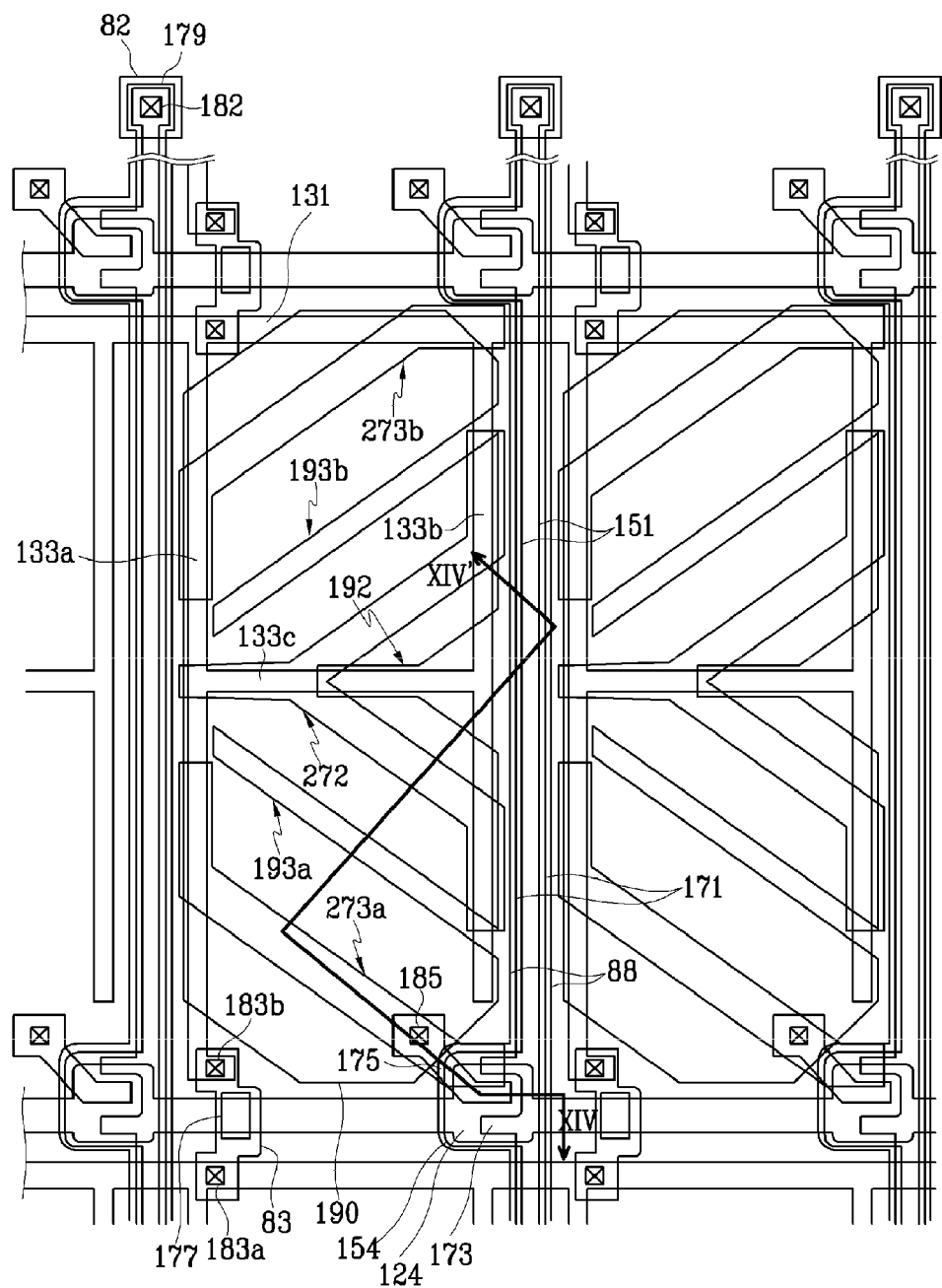
FIG. 13 is a layout view of an LCD including the TFT array panel shown in FIG. 11 and the common electrode panel shown in FIG. 12.
Figure 14:
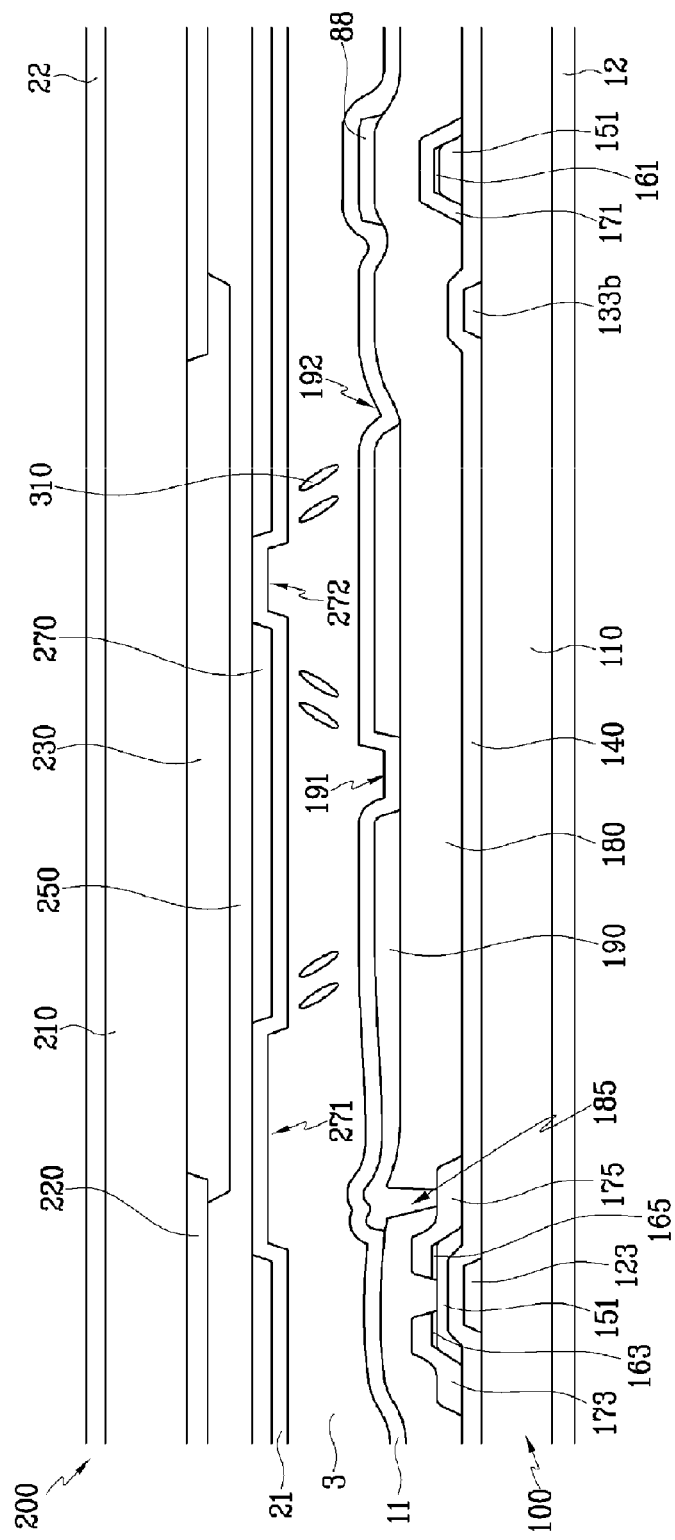
FIG. 14 is a sectional view of the LCD shown in FIG. 13 taken along the line XIV-XIV'.

FIG. 11 is a layout view of a TFT array panel of an LCD according to another embodiment of the present invention, FIG. 12 is a layout view of a common electrode panel of an LCD according to another embodiment of the present invention, FIG. 13 is a layout view of an LCD including the TFT array panel shown in FIG. 11 and the common electrode panel shown in FIG. 12, and FIG. 14 is a sectional view of the LCD shown in FIG. 13 taken along the line XIV-XIV'.

An LCD according to this embodiment includes a TFT array panel 100, a common electrode panel 200, and a LC layer 3 interposed between the panels 100 and 200 and containing a plurality of LC molecules 310 aligned substantially vertical to surfaces of the panels 100 and 200.

The TFT array panel 100 is now described in detail with reference FIGS. 11, 13 and 14.

A plurality of gate lines 121 and a plurality of storage electrode lines 131 are formed on an insulating substrate 110 such as transparent glass.

The gate lines 121 extend substantially in a transverse direction and are separated from each other and transmit gate signals. Each gate line 121 includes a plurality of projections forming a plurality of gate electrodes 124.

Each storage electrode line 131 extends substantially in the transverse direction and includes a plurality of sets of two longitudinal branches forming first and second storage electrodes 133a and 133b and a transverse branch forming a third storage electrode 133c connected between the first storage electrode 133a and the second storage electrode 133b. Each of the first storage electrodes 133a has a free end portion and a fixed end portion connected to the storage electrode line 131, and the fixed end portion has a projection. Each of the third storage electrodes 133c forms a mid-line between two adjacent gate lines 121. The storage electrode lines 131 are supplied with a predetermined voltage such as a common voltage, which is applied to a common electrode 270 on the common electrode panel 200 of the LCD. Each storage electrode line 131 may include a pair of stems extending in the transverse direction.

The gate lines 121 and the storage electrode lines 131 is preferably made of Al containing metal, Ag containing metal, Cu containing metal, Mo containing metal, Cr, Ti or Ta.

In addition, the lateral sides of the gate lines 121 and the storage electrode lines 131 are inclined relative to a surface of the substrate, and the inclination angle thereof ranges about 20-80 degrees.

A gate insulating layer 140 preferably made of silicon nitride (SiNx) is formed on the gate lines 121 and the storage electrode lines 131.

A plurality of semiconductor stripes 151 preferably made of hydrogenated amorphous silicon (abbreviated to "a-Si") or polysilicon are formed on the gate insulating layer 140. Each semiconductor stripe 151 extends substantially in the longitudinal direction and has a plurality of projections 154 branched out toward the gate electrodes 124.

A plurality of ohmic contact stripes and islands 161 and 165 preferably made of silicide or n+ hydrogenated a-Si heavily doped with n type impurity such as phosphorous are formed on the semiconductor stripes 151. Each ohmic contact stripe 161 has a plurality of projections 163, and the projections 163 and the ohmic contact islands 165 are located in pairs on the projections 154 of the semiconductor stripes 151.

The lateral sides of the semiconductor stripes 151 and the ohmic contacts 161 and 165 are inclined relative to a surface of the substrate, and the inclination angles thereof are preferably in a range between about 30-80 degrees.

A plurality of data lines 171, a plurality of drain electrodes 175 separated from the data lines 171, and a plurality of isolated metal pieces 177 are formed on the ohmic contacts 161 and 165 and the gate insulating layer 140.

The data lines 171 for transmitting data voltages extend substantially in the longitudinal direction and intersect the gate lines 121 and the storage electrode lines 131. Each data line 171 is disposed between the first and the second storage electrodes 133a and 133b in adjacent sets of the branches 133a-133c of the storage electrode lines 131 and it includes an end portion 179 having a large area for contact with another layer or an external device. A plurality of branches of each data line 171, which project toward the drain electrodes 175, form a plurality of source electrodes 173. Each drain electrode 175 includes an end portion having a large area for contact with another layer and each source electrode 173 is curved to partly enclose another end portion of the drain electrode 175. A gate electrode 124, a source electrode 173, and a drain electrode 175 along with a projection 154 of a semiconductor stripe 151 form a TFT having a channel formed in the projection 154 disposed between the source electrode 173 and the drain electrode 175.

The metal pieces 177 are disposed on the gate lines 121 near the end portions of the storage electrodes 133a.

The data lines 171, the drain electrodes 175, and the metal pieces 177 are preferably made of refractory metal such as Cr, Mo containing metal, Ta and Ti and they may also have a multilayered structure including a lower film (not shown) preferably made of Mo, Mo alloy or Cr and an upper film (not shown) located thereon and preferably made of Al containing metal.

Like the gate lines 121 and the storage electrode lines 131, the data lines 171 and the drain electrodes 175 have tapered lateral sides, and the inclination angles thereof range about 30-80 degrees.

The ohmic contacts 161 and 165 are interposed only between the underlying semiconductor stripes 151 and the overlying data lines 171 and the overlying drain electrodes 175 thereon and reduce the contact resistance therebetween. The semiconductor stripes 151 include a plurality of exposed portions, which are not covered with the data lines 171 and the drain electrodes 175, such as portions located between the source electrodes 173 and the drain electrodes 175.

A passivation layer 180 is formed on the data lines 171, the drain electrodes 175, and the exposed portions of the semiconductor stripes 151. The passivation layer 180 is preferably made of photosensitive organic material having a good flatness characteristic, low dielectric insulating material having dielectric constant lower than 4.0 such as a-Si:C:O and a-Si:O:F formed by plasma enhanced chemical vapor deposition (PECVD), or inorganic material such as silicon nitride.

The passivation layer 180 has a plurality of contact holes 182 and 185 exposing the end portions 179 of the data lines 171 and the end portions of the drain electrodes 175, respectively. The passivation layer 180 and the gate insulating layer 140 have a plurality of contact holes 183a and 183b exposing portions of the storage electrode lines 131 near the fixed end portions of the first storage electrodes 133a and the projections of the free end portions of the first storage electrodes 133a, respectively. The contact holes 182-185 have a shape of polygon or a circle, and sidewalls of the contact holes 182-185 are tapered. Each of the contact holes 182 exposing the end portions 179 preferably has an area ranging from about 0.5 mm×15 μm to about 2 mm×60 μm.

A plurality of pixel electrodes 190, a plurality of shielding electrodes 88, a plurality of contact assistants 82, and a plurality of overpasses 83, which are preferably made of ITO or IZO, are formed on the passivation layer 180.

The pixel electrodes 190 are physically and electrically connected to the drain electrodes 175 through the contact holes 185 such that the pixel electrodes 190 receive the data voltages from the drain electrodes 175. The pixel electrodes 190 overlap the storage electrode lines 131 including the storage electrodes 133a-133c to form storage capacitors.

Each pixel electrode 190 is chamfered at its left corners and the chamfered edges of the pixel electrode 190 make an angle of about 45 degrees with the gate lines 121.

Each pixel electrode 190 has a center cutout 192, a lower cutout 193a, and an upper cutout 193b, which partition the pixel electrode 190 into a plurality of partitions. The cutouts 192, 193a and 193b substantially have inversion symmetry with respect to a third storage electrode 133c.

The lower and the upper cutouts 193a and 193b obliquely extend approximately from a right edge of the pixel electrode 190 approximately to a left edge of the pixel electrode 190, and they are disposed at lower and upper halves of the pixel electrode 190, respectively, which can be divided by the third storage electrode 133c. The lower and the upper cutouts 193a and 193b make an angle of about 45 degrees to the gate lines 121, and they extend perpendicular to each other.

The center cutout 192 extends along the third storage electrode 133c and has an inlet from the right edge of the pixel electrode 190, which has a pair of inclined edges substantially parallel to the lower cutout 193a and the upper cutout 193b, respectively.

Accordingly, the lower half of the pixel electrode 190 is partitioned into two lower partitions by the lower cutout 193a and the upper half of the pixel electrode 190 is also partitioned into two upper partitions by the upper cutout 193b. The number of partitions or the number of the cutouts is varied depending on the design factors such as the size of pixels, the ratio of the transverse edges and the longitudinal edges of the pixel electrodes, the type and characteristics of the liquid crystal layer 3, and so on.

The shielding electrodes 88 extend along the data lines 171 and fully cover the data lines 171 and the TFTs. The shielding electrodes 88 are supplied with the common voltage and they may be connected to the storage electrode lines 131 through contact holes (not shown) penetrating the gate insulating layer 140 and the passivation layer 180 or connected to short points (not shown) where the common voltage is transmitted from the TFT array panel 100 to the common electrode panel 200. The distance between the shielding electrodes 88 and the pixel electrodes 190 is preferably minimized to minimize the decrease of the aperture ratio.

The contact assistants 82 are connected to the end portions 179 of the data lines 171 through the contact holes 182. The contact assistants 82 protect the end portions 179 and complement the adhesion between the end portions 179 and external devices.

The overpasses 83 cross over the gate lines 121 and they are connected to the exposed portions of the storage electrode lines 131 and the exposed projection of the fixed end portions of the first storage electrodes 133a respectively through the contact holes 183a and 183b opposite each other with respect to the gate lines 121. The overpasses 83 overlaps the metal pieces 177 and they may be electrically connected to the metal pieces 177. The storage electrode lines 131 including the storage electrodes 133a-133c along with the overpasses 83 and the metal pieces 177 are used for repairing defects in the gate lines 121, the data lines 171, or the TFTs. The electrical connection between the gate lines 121 and the storage electrode lines 131 for repairing the gate lines 121 is obtained by illuminating the cross points of the gate lines 121 and the overpasses 83 by a laser beam to electrically connect the gate lines 121 to the overpasses 83. In this case, the metal pieces 177 enhance the electrical connection between the gate lines 121 and the overpasses 83.

The description of the common electrode panel 200 follows with reference to FIGS. 12-14.

A light blocking member 220 is formed on an insulating substrate 210 such as transparent glass. The light blocking member 220 may include a plurality of openings 225 that face the pixel electrodes 190 and it may have substantially the same shape as the pixel electrodes 190. Otherwise, the light blocking member 220 may include linear portions corresponding to the data lines 171 and other portions corresponding to the TFTs.

A plurality of color filters 230 are formed on the substrate 210 and they are disposed substantially in the areas enclosed by the light blocking member 220. The color filters 230 may extend substantially along the longitudinal direction along the pixel electrodes 190. The color filters 230 may represent one of the primary colors such as red, green and blue colors.

An overcoat 250 is formed on the color filters 230.

A common electrode 270 preferably made of transparent conductive material such as ITO and IZO is formed on the overcoat 250.

The common electrode 270 has a plurality of sets of cutouts 272, 273a and 273b.

A set of cutouts 272, 273a and 273b face a pixel electrode 190 and include a center cutout 272, a lower cutout 273a, and an upper cutout 273b. Each of the cutouts 272, 273a and 273b is disposed between adjacent cutouts 192, 193a and 193b of the pixel electrode 190 or between a cutout 193a or 193b and a chamfered edge of the pixel electrode 190. In addition, each of the cutouts 272, 273a and 273b has at least an oblique portion extending parallel to the lower cutout 193a or the upper cutout 193b of the pixel electrode 190. The cutouts 272, 273a and 273b substantially have inversion symmetry with respect to a third storage electrode 133c.

Each of the lower and upper cutouts 273a and 273b includes an oblique portion extending approximately from a left edge of the pixel electrode 190 approximately to a lower or upper edge of the pixel electrode 190, and transverse and longitudinal portions extending from respective ends of the oblique portion along edges of the pixel electrode 190, overlapping the edges of the pixel electrode 190, and making obtuse angles with the oblique portion.

The center cutout 272 includes a central transverse portion extending approximately from the left edge of the pixel electrode 190 along the third storage electrode 133c, a pair of oblique portions extending from an end of the central transverse portion approximately to a right edge of the pixel electrode and making obtuse angles with the central transverse portion, and a pair of terminal longitudinal portions extending from the ends of the respective oblique portions along the right edge of the pixel electrode 190, overlapping the right edge of the pixel electrode 190, and making obtuse angles with the respective oblique portions.

The number of the cutouts 272, 273a and 273b may be varied depending on the design factors, and the light blocking member 220 may also overlap the cutouts 272, 273a and 273b to block the light leakage through the cutouts 272, 273a and 273b.

Homeotropic alignment layers 11 and 21 are coated on inner surfaces of the panels 100 and 200, and polarizers 12 and 22 are provided on outer surfaces of the panels 100 and 200 such that their polarization axes may be crossed and one of the transmissive axes may be parallel to the gate lines 121. One of the polarizers may be omitted when the LCD is a reflective LCD.

The LCD may further include at least one retardation film for compensating the retardation of the LC layer 3.

The LC molecules 310 in the LC layer 3 are aligned such that their long axes are vertical to the surfaces of the panels 100 and 200. The liquid crystal layer 3 has negative dielectric anisotropy.

The cutouts 192, 193a, 193b, 272, 273a and 273b control the tilt directions of the LC molecules in the LC layer 3. That is, the liquid crystal molecules in each region called domain defined by adjacent cutouts 192, 193a, 193b, 272, 273a and 273b or by the cutout 273a or 273b and the chamfered edge of the pixel electrode 190 are tilted in a direction perpendicular to the extension direction of the cutouts 192, 193a, 193b, 272, 273a and 273b. It is apparent that the domains have two long edges extending substantially parallel to each other and making an angle of about 45 degrees with the gate line 121.

The width of the cutouts 192, 193a, 193b, 272, 273a and 273b is preferably in a range between about nine microns to about twelve microns.

At least one of the cutouts 192, 193a, 193b, 272, 273a and 273b can be substituted with protrusions (not shown) or depressions (not shown). The protrusions are preferably made of organic or inorganic material and disposed on or under the field-generating electrodes 190 or 270 and have a width of about five microns to about ten microns.

The distance between an edge of a cutout 192, 193a or 193b and an edge of a cutout 272, 273a or 273b adjacent to the edge of the cutout 192, 193a or 193b and the distance between a chamfered edge of a pixel electrode 190 and an edge of a cutout 272, 273a or 273b adjacent to the edge of the cutout 192, 193a or 193b are preferably in a range between about twelve microns to about twenty microns, more preferably between about seventeen microns to about nineteen microns. This range increased the response time of the liquid crystal to obtain desired transmittance although the aperture ratio decreased.

The shapes and the arrangements of the cutouts 192, 193a, 193b, 272, 273a and 273b may be modified.

An LCD according to another embodiment of the present invention will be described in detail with reference to FIGS. 15-22.

Figure 15:
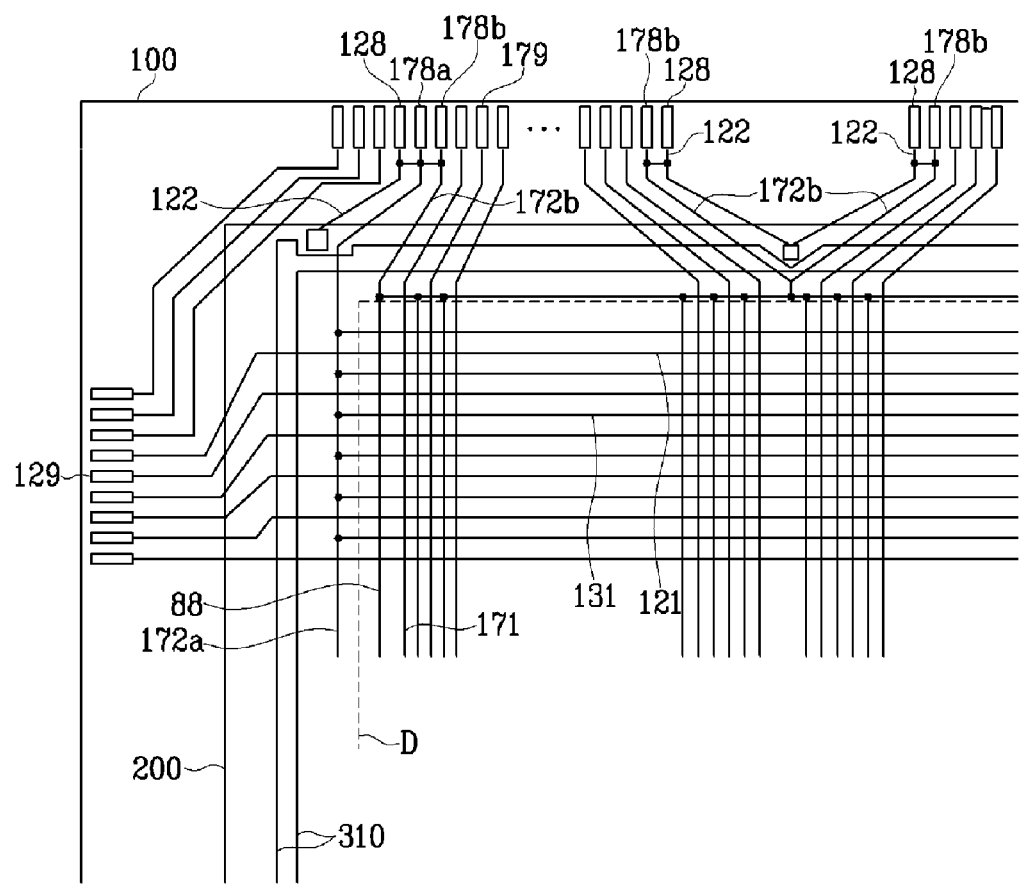
FIG. 15 is a schematic diagram of an LCD according to an embodiment of the present invention.
Figure 16:
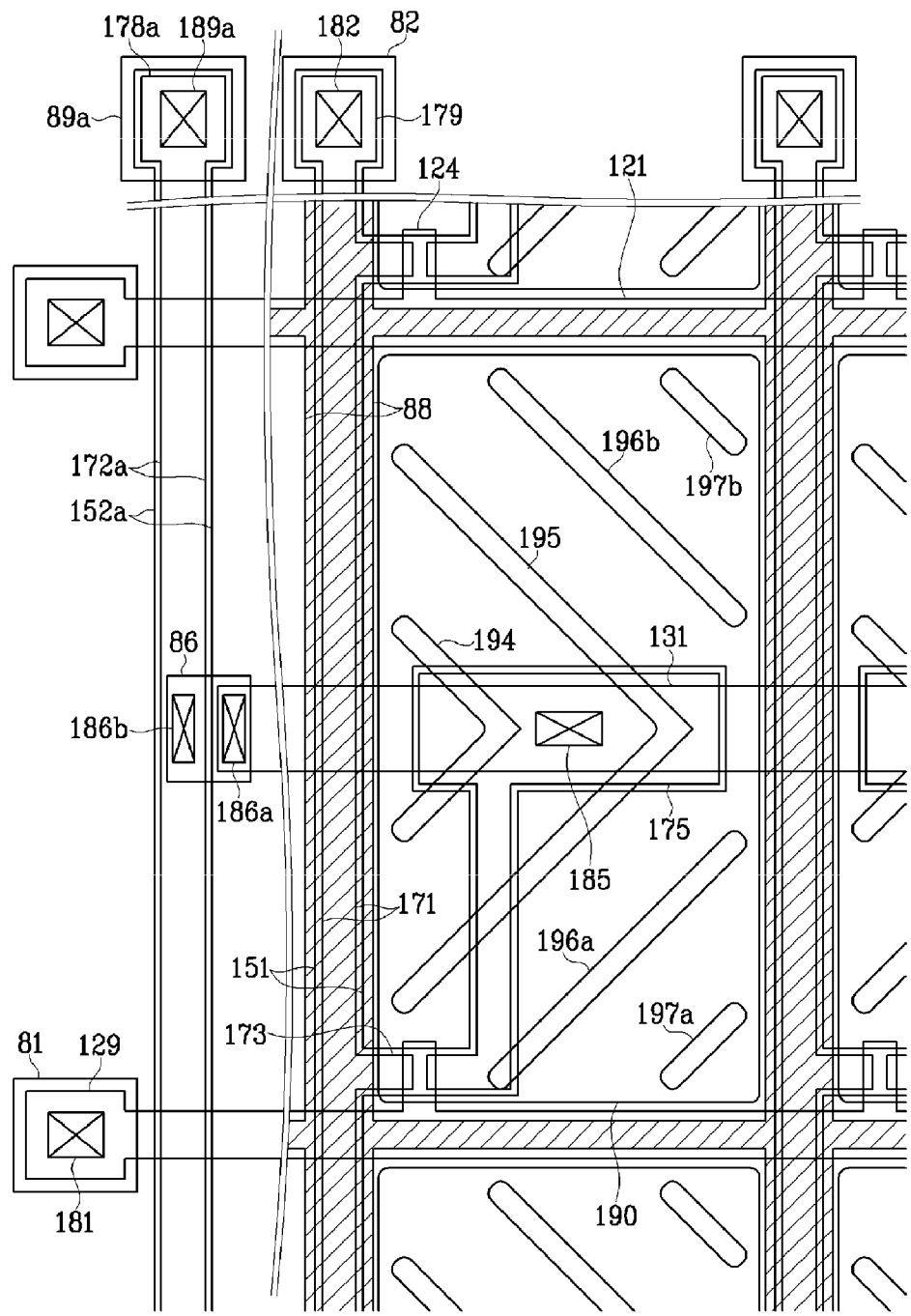
FIG. 16 is an exemplary layout view of a TFT array panel of the LCD shown in FIG. 15.
Figure 17A:
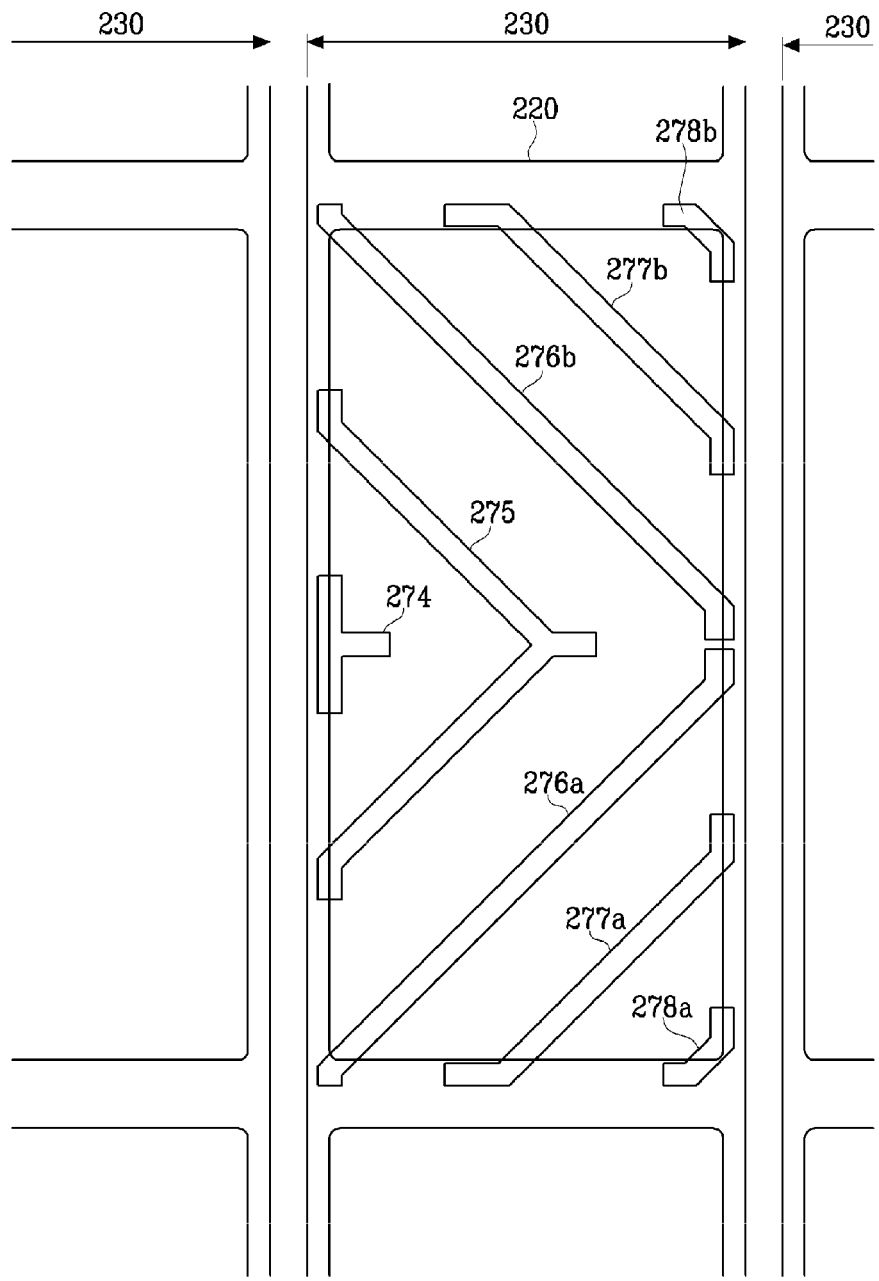
FIGS. 17A and 17B are exemplary layout views of a common electrode panel of the LCD shown in FIG. 15.
Figure 17B:
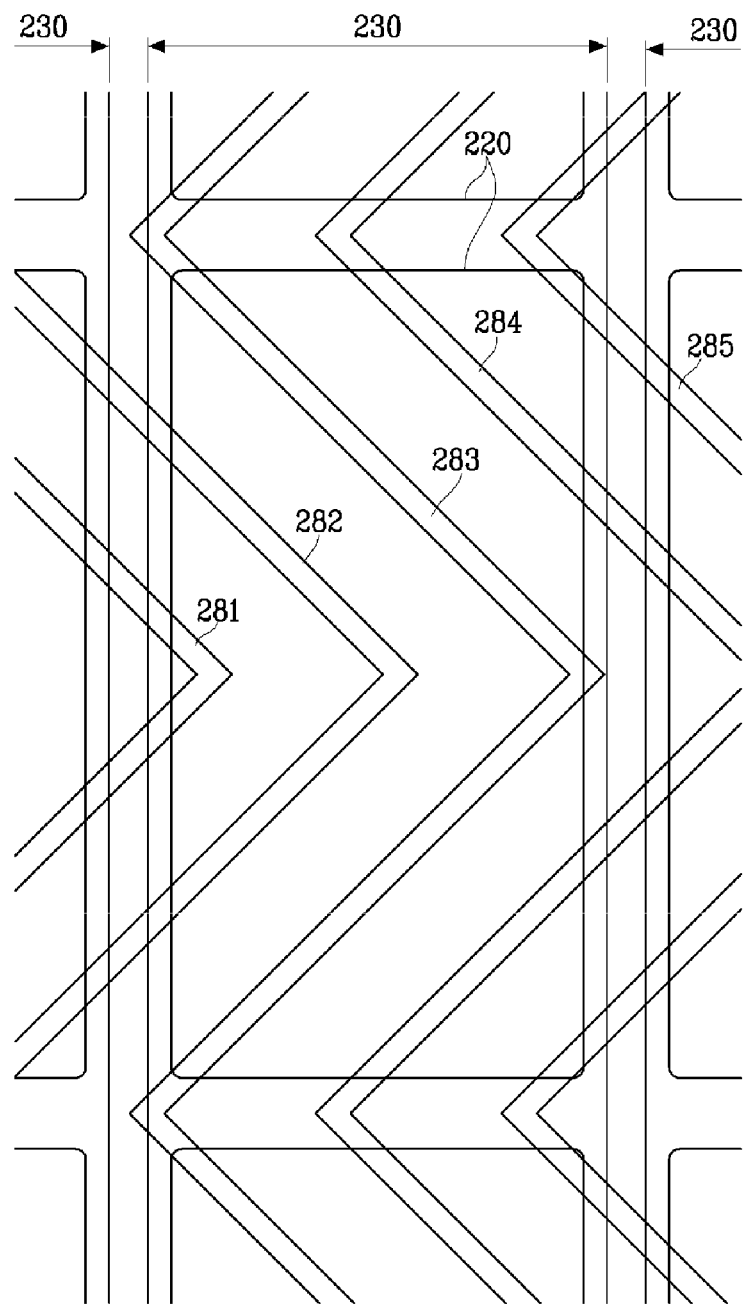
Figure 18A:
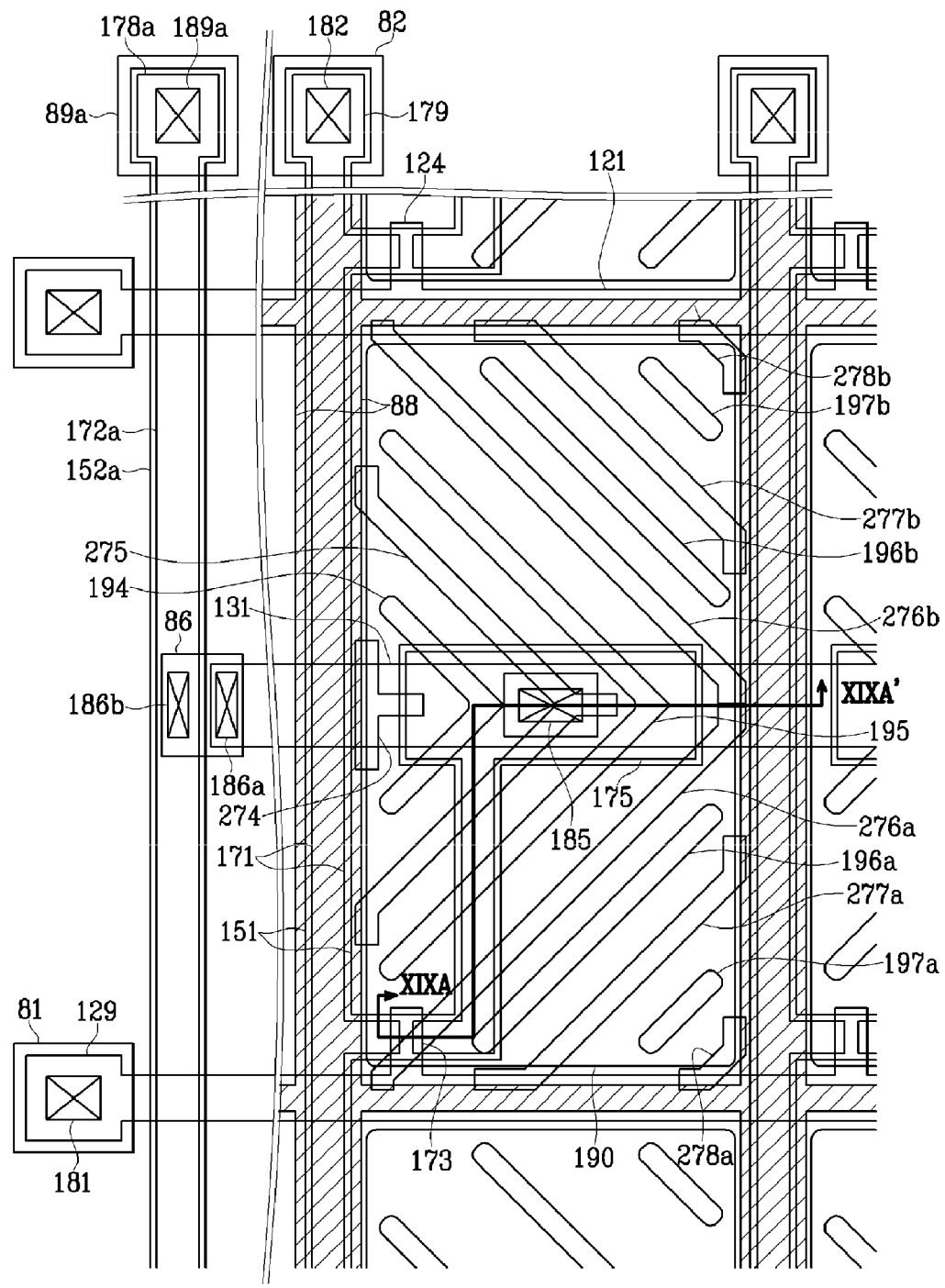
FIG. 18A is a layout view of the LCD including the TFT array panel shown in FIG. 16 and the common electrode panel shown in FIG. 17A.
Figure 18B:
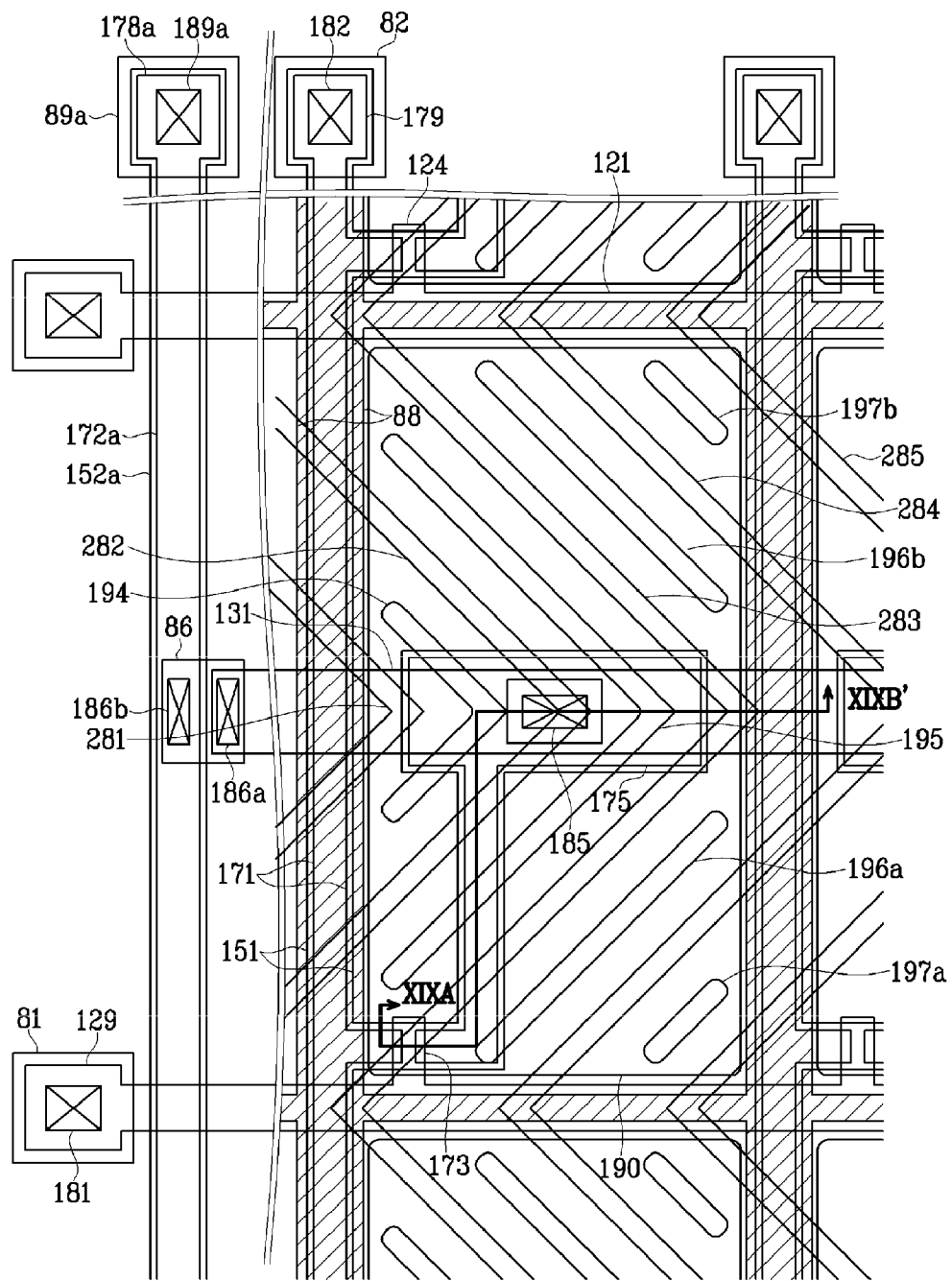
FIG. 18B is a layout view of the LCD including the TFT array panel shown in FIG. 16 and the common electrode panel shown in FIG. 17B.
Figure 19B:
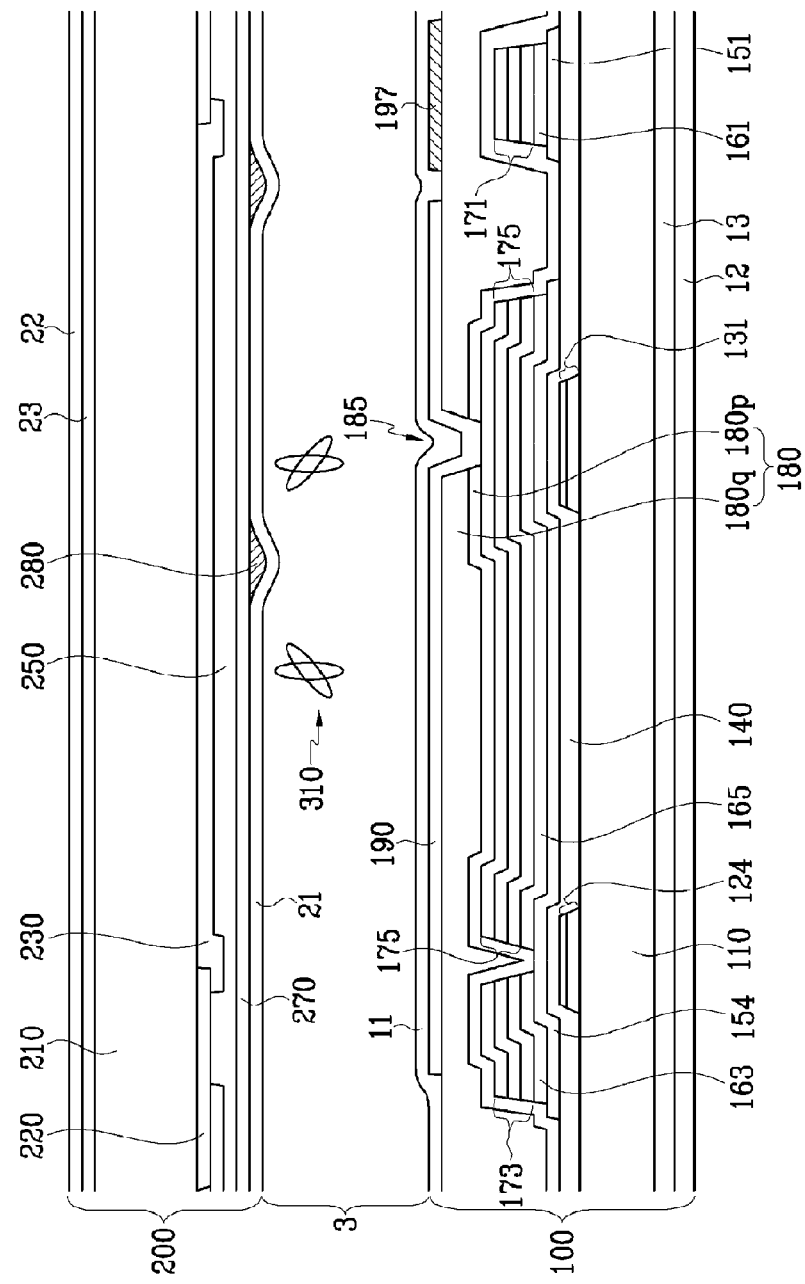
FIG. 19B is a sectional view of the LCD shown in FIG. 18B taken along the line XIXB-XIXB'.
Figure 20:
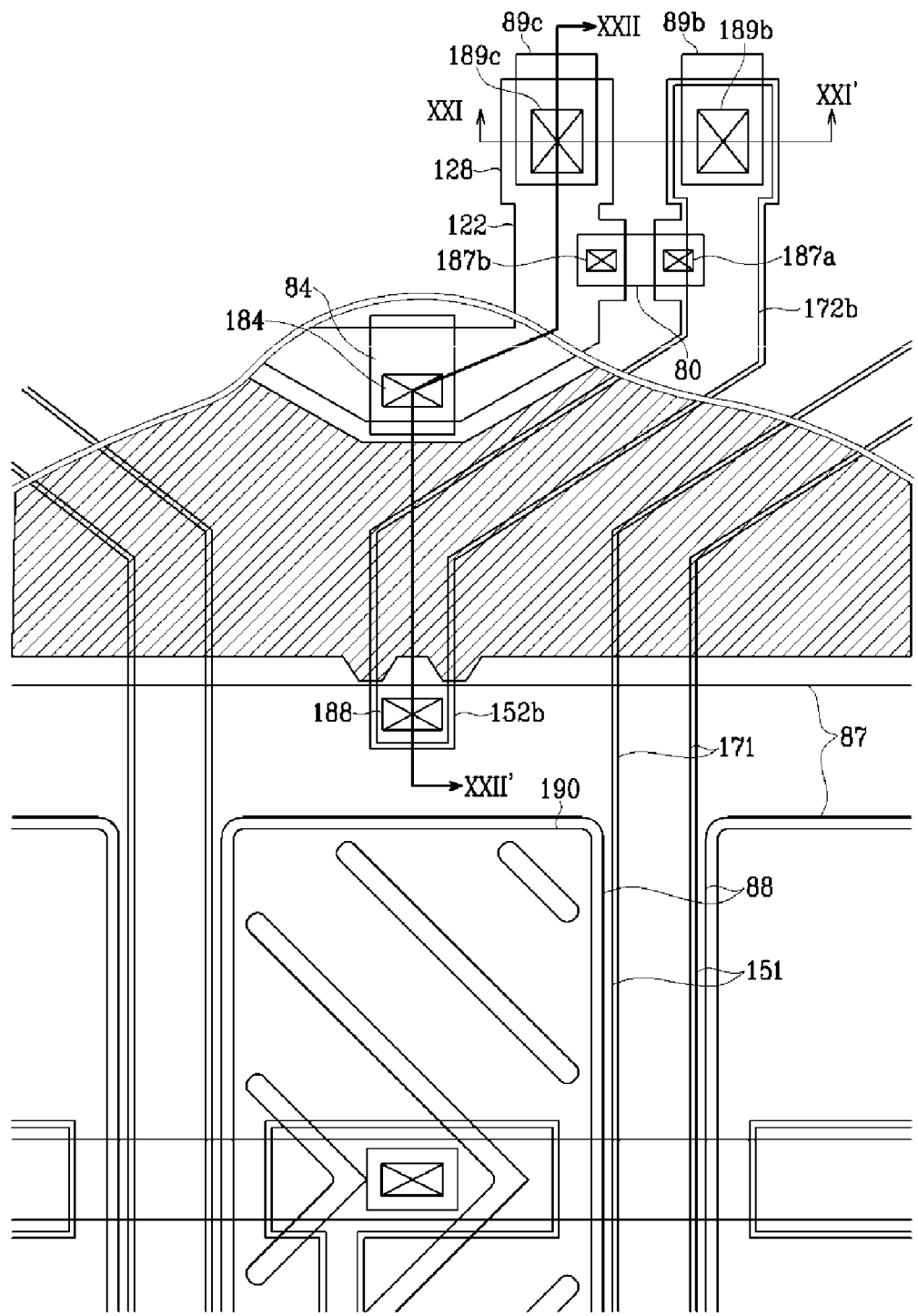
FIG. 20 is an exemplary layout view of a portion of a TFT array panel of the LCD shown in FIG. 15.
Figure 21:
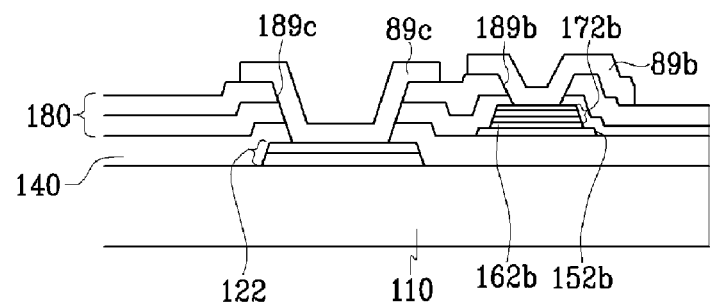
FIG. 21 is a sectional view of the LCD shown in FIG. 20 taken along the line XXI-XXI'.
Figure 22:
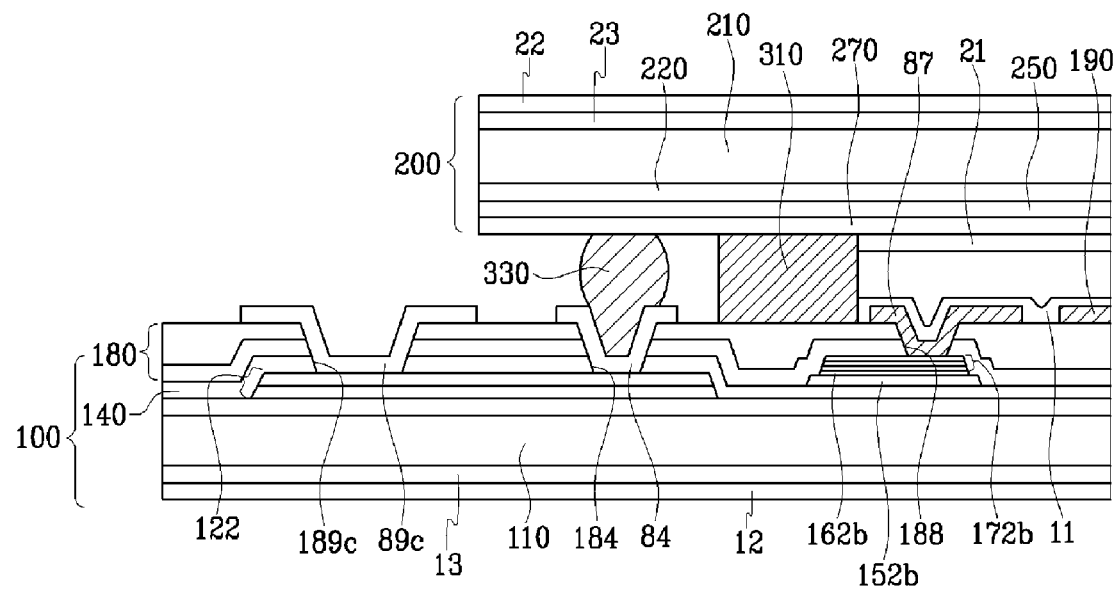
FIG. 22 is a sectional view of the LCD shown in FIG. 20 taken along the line XXII-XXII'.

FIG. 15 is a schematic diagram of an LCD according to an embodiment of the present invention, which illustrates electrical connection between signal lines. FIG. 16 is an exemplary layout view of a TFT array panel of the LCD shown in FIG. 15, FIGS. 17A and 17B are exemplary layout views of a common electrode panel of the LCD shown in FIG. 15, FIG. 18A is a layout view of the LCD including the TFT array panel shown in FIG. 16 and the common electrode panel shown in FIG. 17A, FIG. 18B is a layout view of the LCD including the TFT array panel shown in FIG. 16 and the common electrode panel shown in FIG. 17B, FIG. 19A is a sectional view of the LCD shown in FIG. 18A taken along the line XIXA-XIXA', and FIG. 19B is a sectional view of the LCD shown in FIG. 18B taken along the line XIXB-XIXB'. FIG. 20 is an exemplary layout view of a portions of a TFT array panel of the LCD shown in FIG. 15, FIG. 21 is a sectional view of the LCD shown in FIG. 20 taken along the line XXI-XXI', and FIG. 22 is a sectional view of the LCD shown in FIG. 20 taken along the line XXII-XXII'.

Referring to FIGS. 15-22, an LCD according to this embodiment includes a TFT array panel 100, a common electrode panel 200, a LC layer 3 interposed between the panels 100 and 200, a pair of polarizers 12 and 22 a pair of retardation films 13 and 23 attached on outer surfaces of the panels 100 and 200, a pair of polarizers 12 and 22 attached on outer surfaces of the retardation films 13 and 23, a sealant 310 disposed between the panels 100 and 200 for combining the panels 100 and 200 and for confining the LC layer 3, and a plurality of common voltage transmitting members 330 disposed between the panels 100 and 200 for transmitting a common voltage from the TFT array panel 100 to the common electrode panel 200. The common voltage transmitting members 330 may include conductive balls made of Ag paste or made of organic elastic material plated with metal such as Au.

Referring FIG. 15, the common electrode panel 200 is smaller than the TFT array panel 100 and thus left and upper areas of the TFT array panel 100 are exposed. The sealant 310 extends along edges of the common electrode panel 200 and an area enclosed by the sealant 310 is nearly occupied by a display area D, while the other areas except for the display area D is referred to as a peripheral area.

Layered structures of the panels 100 and 200 according to this embodiment are almost the same as those shown in FIGS. 11-14.

Regarding the TFT array panel 100, a plurality of gate lines 121 including gate electrodes 124 and end portions 129 and a plurality of storage electrode lines 131 are formed on a substrate 110, and a gate insulating layer 140, a plurality of semiconductor stripes 151 including projections 154, and a plurality of ohmic contact stripes 161 including projections 163 and a plurality of ohmic contact islands 165 are sequentially formed thereon. A plurality of data lines 171 including source electrodes 173 and end portions 179 and a plurality of drain electrodes 175 are formed on the ohmic contacts 161 and 165, and a passivation layer 180 is formed thereon. A plurality of contact holes 181, 182 and 185 are provided at the passivation layer 180 and the gate insulating layer 140. A plurality of pixel electrodes 190, a plurality of shielding electrodes 88, and a plurality of contact assistants 81 and 82 are formed on the passivation layer 180, and an alignment layer 11 is coated thereon.

Regarding the common electrode panel 200, a light blocking member 220, a plurality of color filters 230, an overcoat 250, a common electrode 270, and an alignment layer 21 are formed on an insulating substrate 210.

Referring to FIG. 15, the TFT array panel 100 further includes a plurality of signal lines for transmitting various signals as well as the gate lines 121, the data lines 171, the storage electrode lines 131, the shielding electrodes 88. The plurality of signal lines include a plurality of common electrode voltage supplying lines 122 for transmitting a voltage to the common electrode 270, a storage electrode voltage supplying line 172a for transmitting a voltage to the storage electrode lines 131, and a plurality of shielding electrode voltage supplying lines 172b for transmitting a voltage to the shielding electrodes 88. The voltage supplying lines 122, 172a and 172b are electrically connected to each other, and include input terminals 128, 178a and 178b connected to other layers or external devices for receiving voltages. The end portions 129 of the gate lines 121, etc., are arranged in series near the left edge of the TFT array panel 100, while the end portions 179 of the data lines 171, the input terminals 128, 178a and 178b of the voltage supplying lines 122, 172a and 172b, etc., are arranged in series near the upper left edge of the TFT array panel 100.

Referring to FIGS. 16-19B, the storage electrode lines 131 are merely linear and have no branch and pass through nearly centers of the pixel electrodes 190 in a transverse direction.

The storage electrode voltage supplying line 172a includes the same layer as the data lines 171, and it extends from its input terminal 178a substantially in a longitudinal direction to cross over the gate lines 121 near the end portions 129 of the gate lines 121 and end portions of the storage electrode lines 131. The passivation layer 180 has a plurality of contact holes 186b arranged along the length of the storage electrode voltage supplying line 172a and exposing portions of the storage electrode voltage supplying line 172a and a contact holes 189a exposing the input terminal 178a of the storage electrode voltage supplying line 172a. In addition, the passivation layer 180 and the gate insulating layer 140 have a plurality of contact holes 186a exposing end portions of the storage electrode lines 131. A contact assistant 89a connected to the input terminal 178a of the storage electrode voltage supplying line 172a through the contact hole 189a and a plurality of connecting members 86 connected to the storage electrode lines 131 and the storage electrode voltage supplying line 172a through the contact holes 186a and 186b are formed on the passivation layer 180.

Referring FIGS. 20-22, the common electrode voltage supplying lines 122 includes the same layer as the gate lines 121 and they extend from their input terminals 128 to reach the common voltage transmitting members 330 disposed near the sealant 310 but they do not meet the sealant 310. Adjacent two of the common electrode voltage supplying lines 122 extend to one of the common voltage transmitting members 330, which is nearly equidistant from them, to form a V shape, but one common voltage transmitting member 330 may be connected to only one of the common electrode voltage supplying lines 122 extending straight in the longitudinal direction. The passivation layer 180 and the gate insulating layer 140 have a plurality of contact holes 189c exposing the input terminals 128 of the common electrode voltage supplying lines 122 and a plurality of contact holes 184 exposing portions (referred to as output terminals hereinafter) of the common electrode voltage supplying lines 122 disposed under the common voltage transmitting members 330. A plurality of contact assistants 89c connected to the input terminals 128 of the common electrode voltage supplying lines 122 through the contact holes 189c and a plurality of contact assistants 84 connected to the output terminals of the common electrode voltage supplying lines 122 through the contact holes 184 are formed on the passivation layer 180. The contact assistants 84 contact the common voltage transmitting members 330.

Describing the shielding electrodes 88 and related configurations before describing the shielding electrode voltage supplying lines 172b, the TFT array panel 100 further includes a shielding electrode connection 87 that is disposed near the sealant 310, extends substantially in the transverse direction, is connected to the shielding electrodes 88, and includes the same layer as the shielding electrodes 88. The shielding electrodes 88 are connected to each other through connecting members extending along the gate lines 121. The shielding electrode voltage supplying lines 172b include the same layer as the data lines 171, and they run from their input terminals 178b, pass through the sealant 310, and reach the shielding electrode connection 87. The passivation layer 180 has a plurality of contact holes 189b exposing the input terminals 178b of the shielding electrode voltage supplying lines 172b and a plurality of contact holes 188 exposing portions (referred to as output terminals hereinafter) of the shielding electrode voltage supplying lines 172b disposed under the shielding electrode connection 87. The shielding electrode voltage supplying lines 172b and the shielding electrode connection 87 are connected to each other through the contact holes 188. A plurality of contact assistants 89b connected to the input terminals 178b of the shielding electrode voltage supplying lines 172b through the contact holes 189b are formed on the passivation layer 180.

The common electrode voltage supplying lines 122 and the shielding electrode voltage supplying lines 172b include projections for mutual connections. The passivation layer 180 and the gate insulating layer 140 have a plurality of contact holes 187b exposing the projections of the common electrode voltage supplying lines 122, and the passivation layer 180 has a plurality of contact holes 187a exposing projections of the shielding electrode voltage supplying lines 172b. A plurality of connecting members 80 connected to the common electrode voltage supplying lines 122 and the shielding electrode voltage supplying lines 172b through the contact holes 187a and 187b are formed on the passivation layer 180. The storage electrode voltage supplying line 172a may be connected to the common electrode voltage supplying lines 122 or the shielding electrode voltage supplying lines 172b in a similar way.

The voltage supplying lines 122, 172a and 172b may include the same layer as any of the gate lines 121 and the data lines 171.

In particular, when the common electrode voltage supplying lines 122 and the shielding electrode voltage supplying lines 172b are disposed on the same layer, they may be directly connected to each other without connecting members 80. In addition, the common electrode voltage supplying lines 122 and the shielding electrode voltage supplying lines 172b, even though they are separated from each other on the substrate 110, are electrically connected to each other via external devices such as conductive films or a semiconductor chips for driving the panels 100 and 200. Furthermore, the common electrode voltage supplying lines 122 and the shielding electrode voltage supplying lines 172b are connected through the same contact holes. The storage electrode voltage supplying line 172a may be connected to the common electrode voltage supplying lines 122 or the shielding electrode voltage supplying lines 172b in a similar way.

At least one of the storage electrode voltage supplying line 172a, the common electrode voltage supplying lines 122, and the shielding electrode voltage supplying lines 172b may be electrically separated from the others and supplied with a separated voltage.

The common electrode voltage supplying lines 122 may be supplied with different magnitudes of the common voltage for compensating the signal delay of the gate signals at places far from the end portions 129 of the gate lines 121. In this case, the storage electrode voltage supplying line 172a and the shielding electrode voltage supplying lines 172b may be supplied with voltages having position-dependent magnitudes.

Additional common voltage transmitting members 330 may be disposed near the end portions 129 of the gate lines 121 opposite the end portions 179 of the data lines 171. At this time, to the additional common voltage transmitting members 330 may be connected to the common electrode voltage supplying lines 122 that are extended thereto or to the storage electrode voltage supplying line 172a. The shielding electrodes 88 may be supplied with the voltages in a similar way.

The source electrodes 173 and the drain electrodes 175 are disposed opposite each other with respect to the gate electrodes 124, and the drain electrodes 175 extend upward and include expansions overlapping the storage electrode lines 131. The contact holes 185 are disposed on the expansions of the drain electrodes 175.

The TFT array panel 100 further includes a plurality of semiconductor stripes 152a and 152b disposed under the voltage supplying lines 172a and 172b and a plurality of ohmic contact 162a and 162b disposed thereon.

The semiconductor stripes 151 extend along the drain electrodes 175, and the semiconductor stripes 151, 152a and 152b are slightly wider than the ohmic contacts 161, 162a, 162b and 165 and the signal lines 171, 172a and 172b disposed thereon. However, the width of the semiconductor stripes 151, 152a and 152b may be equal to or smaller than that of the signal lines 171, 172a and 172b like those shown in FIGS. 11-14.

The semiconductor may be disposed only between the source electrodes 173 and the drain electrodes to have a shape of islands.

The gate lines 121, the storage electrode lines 131, and the common electrode voltage supplying lines 121 include a lower film having low resistivity and an upper film having good contact characteristics such as refractory metal. The data lines 171, the drain electrodes 175, and the voltage supplying lines 172a and 172b include a triple-layered structure preferably including a Mo lower film, an Al intermediate film, and a Mo upper film. However, they may have various layered structure.

The passivation layer 180 include a lower film 180p preferably made of inorganic material and an upper film 180q preferably made of organic material having good flatness characteristic. The upper film 180q may have dielectric constant lower than about 3.0, and thickness of the lower film 180p is equal to about 300 Å-600 Å, while thickness of the upper film 180q is larger than about 0.7 microns.

The color filters 230 may be provided on the TFT array panel 100 rather than on the common electrode panel 200, and in this case, the color filters 230 are preferably disposed between the lower film 180p and the upper film 180q. In addition, one of the lower film 180p and the upper film 180q may be omitted.

As described above, the plurality of contact holes 181, 182, 184, 185, 186a, 186b, 187a, 187b, 188 and 189a-189c are provided at the passivation layer 180 and the gate insulating layer 140. The contact holes 181, 182, 184, 185, 186a, 186b, 187a, 187b, 188 and 189a-189c are roughly classified into two groups. The contact holes 181, 182 and 189a-189c disposed near the edges of the TFT array panel 100 is provided for receiving various signals from external devices such as driving circuits formed in semiconductor chips, and the remaining contact holes 184, 185, 186a, 186b, 187a, 187b and 188 are provided for electrically connecting the signal lines 121, 122, 131, 171, 172a and 172b and the electrodes 88, 175 and 270. In particular, the signal lines 121, 122 and 131 disposed on the same layer as the gate lines 121 and the signal lines 171, 172a and 172b disposed on the same layer as the data lines 171 are connected to each other via the connecting members 80 and 86 disposed on the pixel electrodes 190. Additional connecting members (not shown) may be provided for connecting the gate lines 121 and the data lines 171 to shorting bars (not shown) for electrostatic discharge protection or to test signal lines (not shown).

The upper film 180q of the passivation layer 180 may be made of photosensitive organic film, and in this case the contact holes 181, 182, 184, 185, 186a, 186b, 187a, 187b, 188 and 189a-189c can be formed by the process described with reference to FIGS. 1-8.

For increased contact reliability of the contact assistants 81, 82 and 89a-89c disposed in the peripheral area, portions of the upper film 180q disposed in the peripheral area may be thinner than those in the display area D. For this purpose, a photo-mask (not shown) for patterning the upper film 180q may be designed to have a slit area or a translucent area facing the peripheral area.

In the meantime, the shielding electrodes 88 are preferably narrower than the gate lines 121 and wider than the data lines 171. In particular, the width of the shielding electrodes 88 is preferably about twice that of the data lines 171, for example, the width of the shielding electrodes 88 may be about thirteen microns when the width of the data lines 171 is about six microns. However, the shielding electrodes 88 may be narrower than the data lines 171.

The number of the cutouts 194, 195, 196a, 196b, 197a and 197b of the pixel electrodes 190 and the number of the cutouts 274, 275, 276a, 276b, 277a, 277b, 278a and 278b of the common electrode 270 in the LCD shown in FIGS. 17A, 18A and 19A are larger than those in the LCD shown in FIGS. 11-14. For illustrative convenience, FIG. 19A do not show all the cutouts 194, 195, 196a, 196b, 197a, 197b, 274, 275, 276a, 276b, 277a, 277b, 278a and 278b, but shows only a few of the cutouts of the common electrode 270, which are denoted as reference character c.

The LCD shown in FIGS. 17B, 18B and 19B has a plurality of protrusions 281-285 having inclined surfaces on the common electrode 270 instead of the cutouts at the common electrode 270. The protrusions 281-285 have nearly the same planar shape as the cutouts 274, 275, 276a, 276b, 277a, 277b, 278a and 278b shown in FIGS. 17A, 18A and 19A, but they are connected to each other to form a plurality of uniform curved stripes rather than separated from each other between the pixel electrodes 190. On the contrary, the cutouts 274, 275, 276a, 276b, 277a, 277b, 278a and 278b may not be connected to each other for preventing the increase of the resistance of the common electrodes 270 and for obtaining signal paths for the common voltage. For illustrative convenience, FIG. 19B do not show all the cutouts 194, 195, 196a, 196b, 197a and 197b the protrusion 281-285, but shows only a few of the protrusions on the common electrode panel 200, which are denoted as reference numeral 280.

The protrusions 281-285 may be formed by uniformly coating a photosensitive film using spin coating, slit coating, inkjet injection, or printing on an entire surface of the common electrode 270 and by light exposure and development with a normal photo-mask. Alternatively, the protrusions 281-285 may be directly formed by screen printing, laser transcription, etc.

The LC molecules 310 are pre-tilted perpendicular to the inclined surfaces of the protrusions 281-285 and thus the tilt directions upon application of electric field are determined. Accordingly, a plurality of domains are divided with respect to the protrusions 281-285.

Many of the above-described features of the LCD shown in FIGS. 11-14 may be appropriate to the LCD shown in FIGS. 15-22.

An LCD according to another embodiment of the present invention will be described in detail with reference to FIGS. 23-26.

Figure 23:
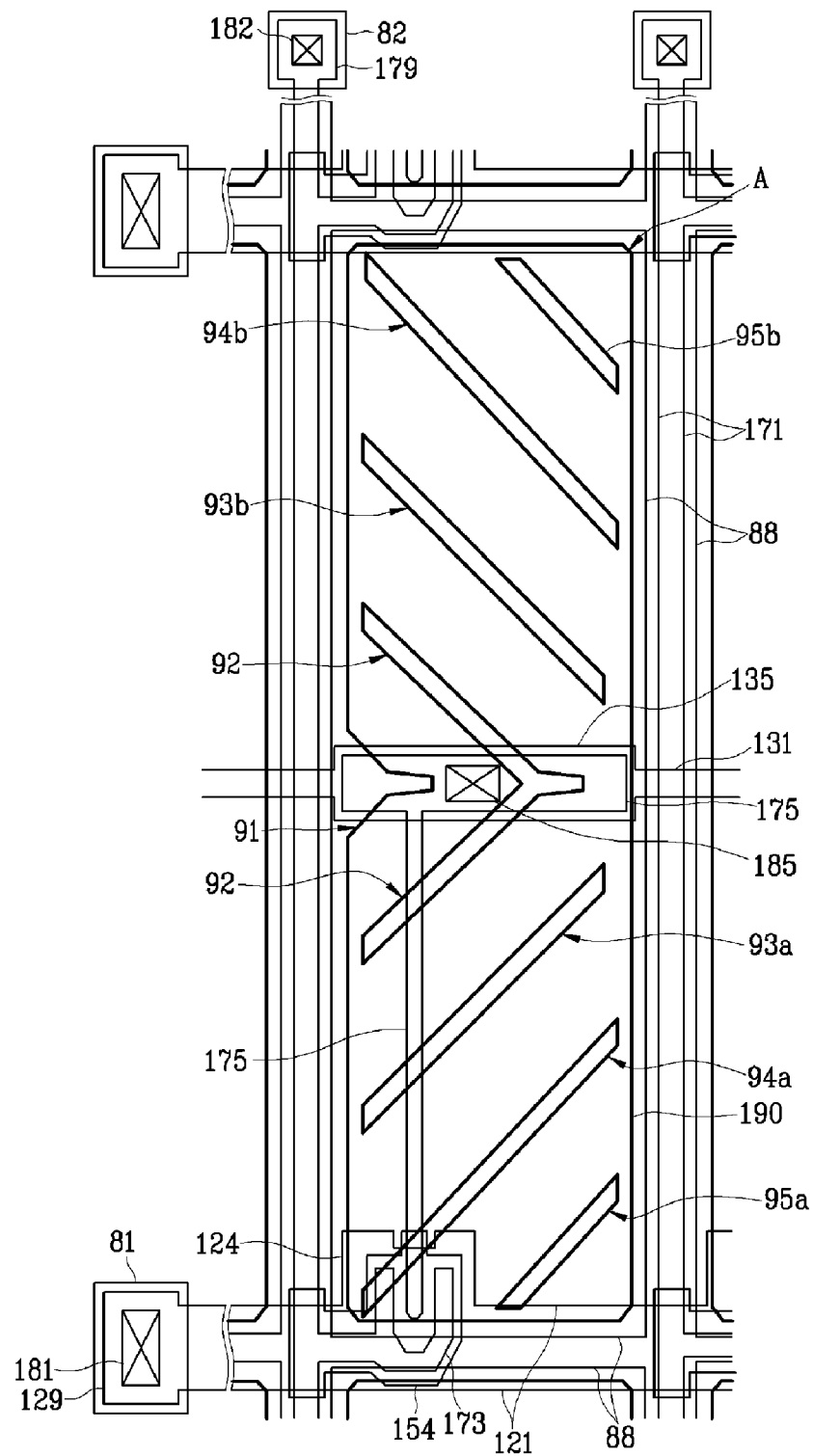
FIG. 23 is a layout view of a TFT array panel of an LCD according to another embodiment of the present invention.
Figure 24:
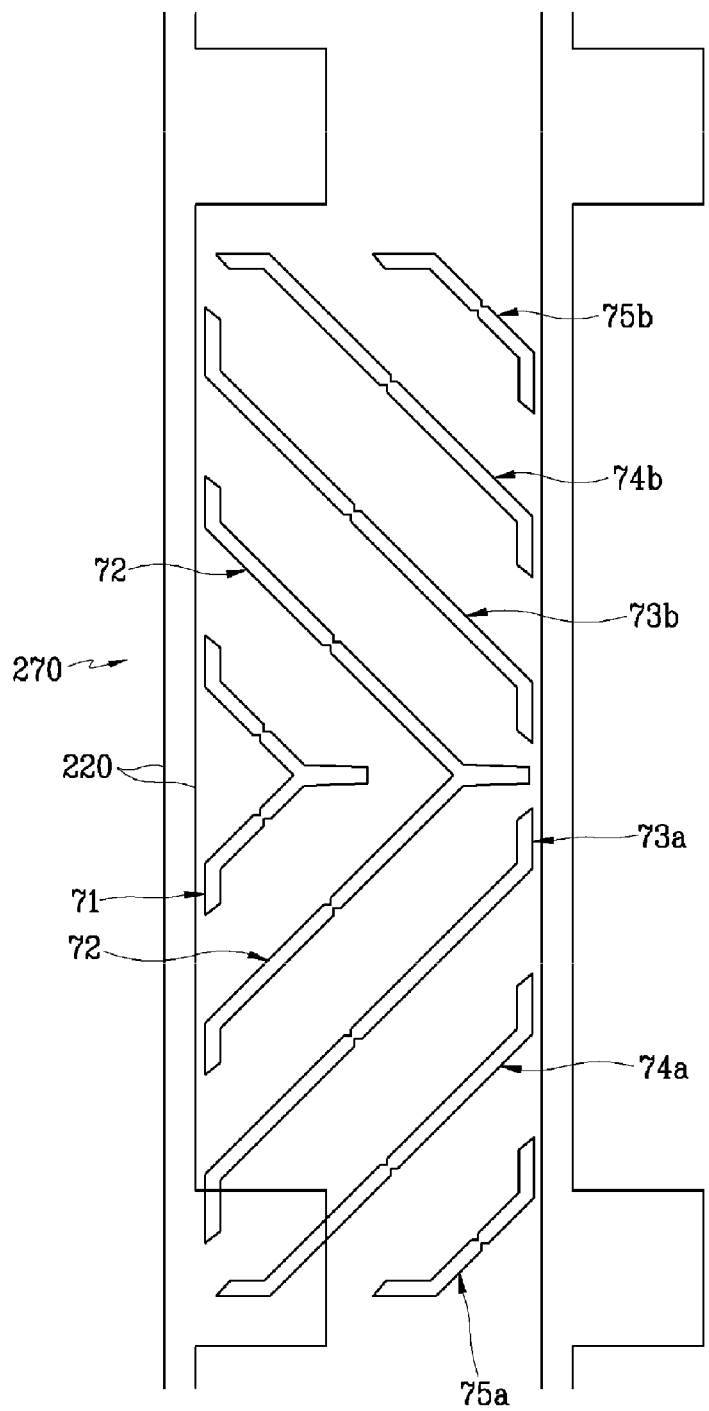
FIG. 24 is a layout view of a common electrode panel of an LCD according to another embodiment of the present invention.
Figure 25:
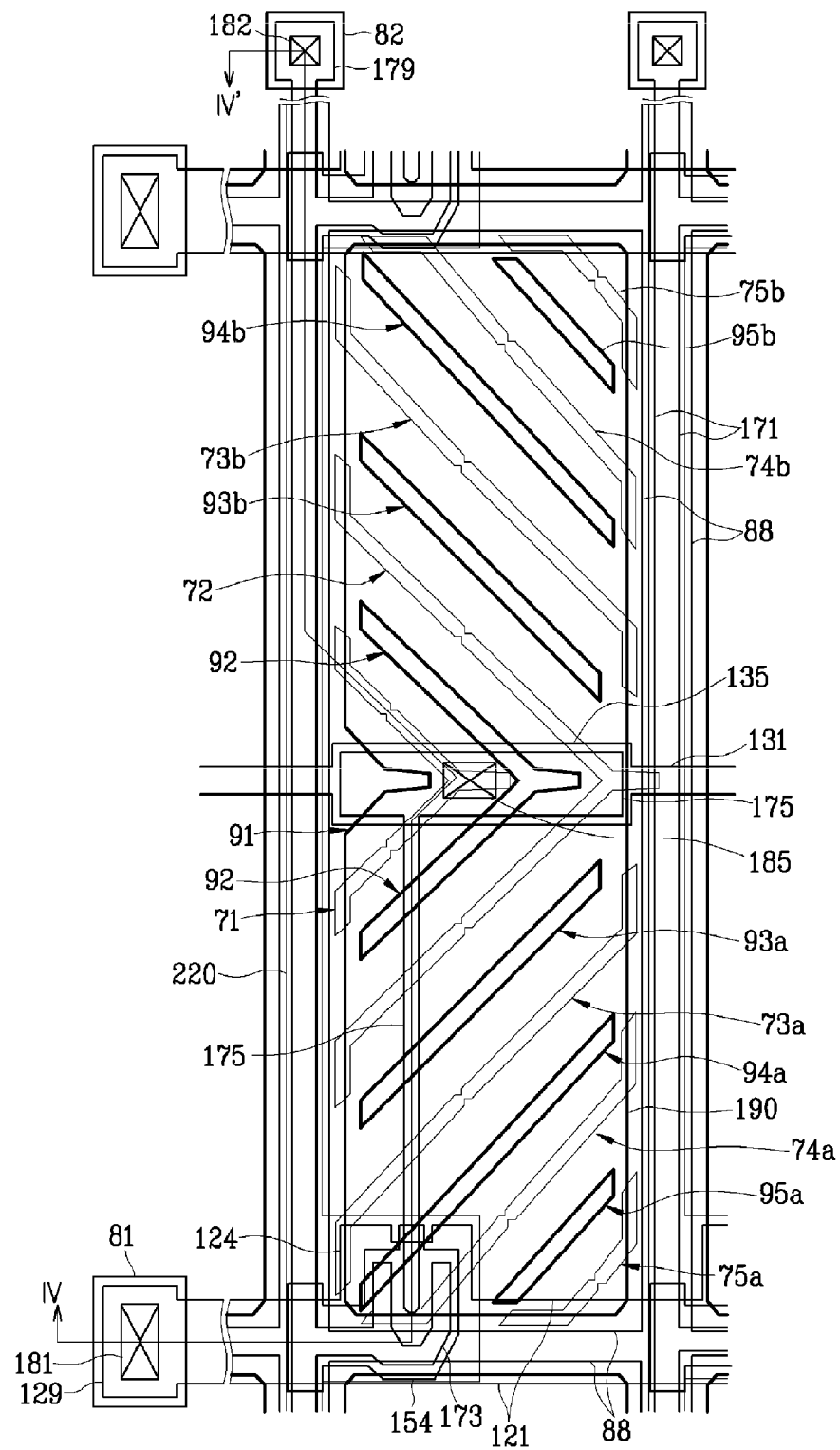
FIG. 25 is a layout view of an LCD including the TFT array panel shown in FIG. 23 and the common electrode panel shown in FIG. 24.
Figure 26:
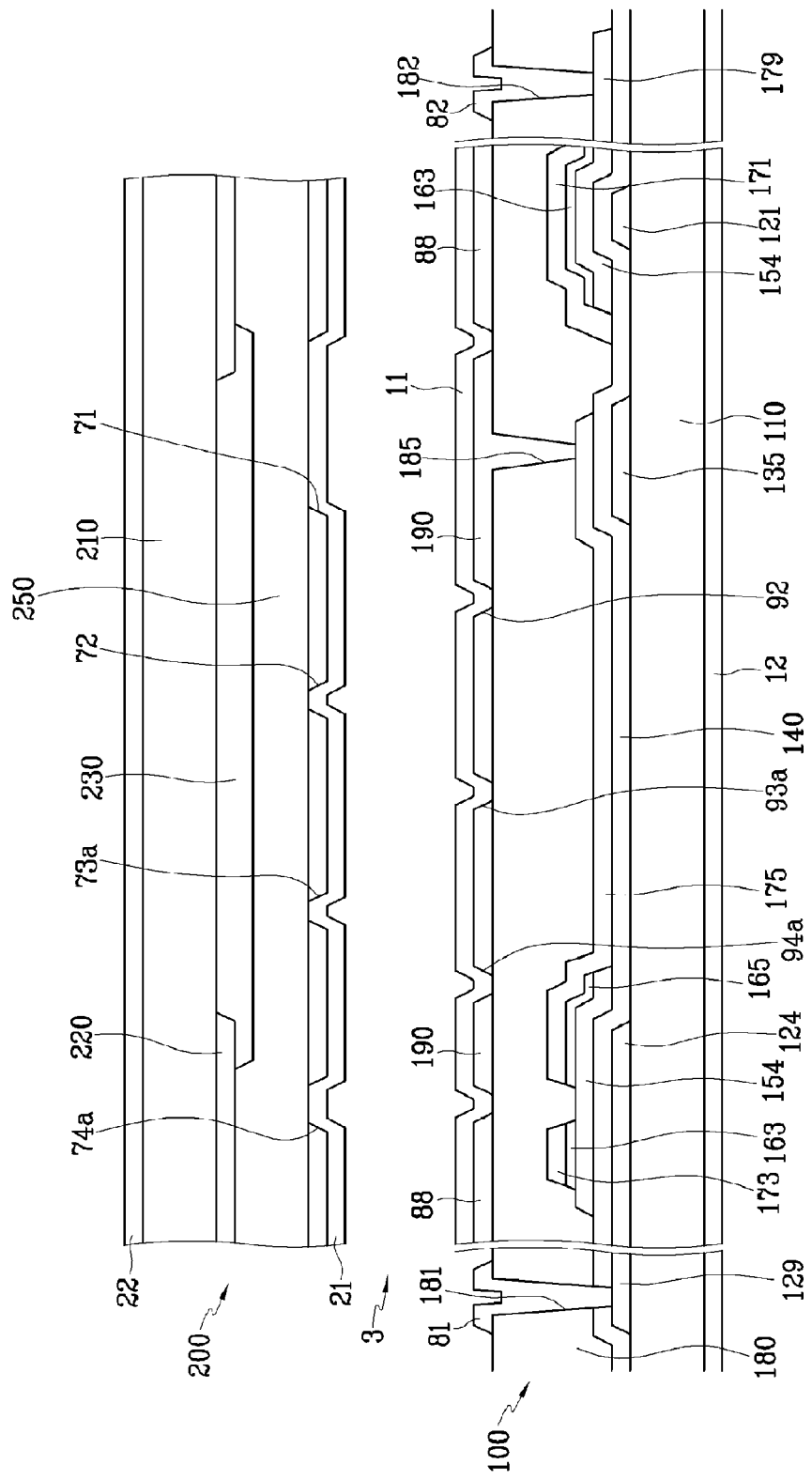
FIG. 26 is a sectional view of the LCD shown in FIG. 25 taken along the line XXVI-XXVI'.

FIG. 23 is a layout view of a TFT array panel of an LCD according to another embodiment of the present invention, FIG. 24 is a layout view of a common electrode panel of an LCD according to another embodiment of the present invention, FIG. 25 is a layout view of an LCD including the TFT array panel shown in FIG. 23 and the common electrode panel shown in FIG. 24, and FIG. 26 is a sectional view of the LCD shown in FIG. 25 taken along the line XXVI-XXVI'.

Referring to FIGS. 23-26, an LCD according to this embodiment includes a TFT array panel 100, a common electrode panel 200, a LC layer 3 interposed between the panels 100 and 200, and a pair of polarizers 11 and 21 attached to outer surfaces of the panels 100 and 200.

Layered structures of the panels 100 and 200 according to this embodiment are almost the same as those shown in FIGS. 16, 17A, 18A and 19A.

Regarding the TFT array panel 100, a plurality of gate lines 121 including gate electrodes 124 and a plurality of storage electrode lines 131 are formed on a substrate 110, and a gate insulating layer 140, a plurality of semiconductors 154, and a plurality of ohmic contacts 163 and 165 are sequentially formed thereon. A plurality of data lines 171 including source electrodes 173 and a plurality of drain electrodes 175 are formed on the ohmic contacts 161 and 165 and the gate insulating layer 140, and a passivation layer 180 is formed thereon. A plurality of contact holes 181, 182 and 185 are provided at the passivation layer 180 and the gate insulating layer 140. A plurality of pixel electrodes 190, a plurality of shielding electrodes 88, and a plurality of contact assistants 81 and 82 are formed on the passivation layer 180, and an alignment layer 11 is coated thereon.

Regarding the common electrode panel 200, a light blocking member 220, a plurality of color filters 230, an overcoat 250, a common electrode 270, and an alignment layer 21 are formed on an insulating substrate 210.

Different from the LCD shown in FIGS. 16, 17A, 18A and 19A, each of the pixel electrodes 190 has four chamfered corners A forming oblique edges. The length of the oblique edges is preferably equal to about four to ten microns, and in particular, it is preferably larger than the resolution of a light exposer used in a photolithography step for forming the pixel electrodes 190 and the shielding electrodes 88. Accordingly, the probability that conductive remnants are remained near the corners A of the pixel electrodes 190 is significantly reduced to prevent the short circuit between the pixel electrodes 190 and the shielding electrodes 88 and to allow the close distance between the pixel electrodes 190 and the shielding electrodes 88.

Furthermore, when the pixel electrodes 190 and the shielding electrodes 88 are short-circuited near the corners A of the pixel electrodes 190, the short-circuited position can be easily detected using a low magnification optical device and the short-circuit can be easily repaired using laser beam since the distance between the shielding electrodes 88 and the pixel electrodes 190 are large at the corners A.

In addition, the arrangements and the shapes of cutouts 91, 92, 93a, 93b, 94a, 94b, 95a and 95b of the pixel electrodes 190 and the cutouts 71, 72, 73a, 73b, 74a, 74b, 75a and 75b of the common electrode 270 are slightly different. In particular, the cutouts 71, 72, 73a, 73b, 74a, 74b, 75a and 75b of the common electrode 270 has notches for controlling the alignments of the LC molecules 310 in the cutouts 71, 72, 73a, 73b, 74a, 74b, 75a and 75b.

In the meantime, the source electrodes 173 have shapes of character U enclosing end portions of the drain electrodes 175.

The semiconductors 154 and the ohmic contacts 163 and 165 have shape of islands and they are mainly disposed between the source electrodes 173 and the drain electrodes 175. The semiconductors 154 and the ohmic contacts 163 and 165 extend to intersections of the gate lines 121 and the data lines 171 and the drain electrodes 175 to smooth surface profiles under the data lines 171 and the drain electrodes 175, thereby preventing disconnections of the data lines 171 and the drain electrodes 175.

The storage electrodes lines 131 have expansions overlapping expansions of the drain electrodes 175 for increasing storage capacitance.

In addition, the gate lines 121, the storage electrodes lines 131, the data lines 171, the drain electrodes 175, and the passivation layer 180 have a single layered structure unlike those shown in FIGS. 16, 17A, 18A and 19A.

Many of the above-described features of the LCD shown in FIGS. 15-22 may be appropriate to the LCD shown in FIGS. 23-26.

An LCD according to another embodiment of the present invention will be described in detail with reference to FIGS. 27 and 28.

Figure 27:
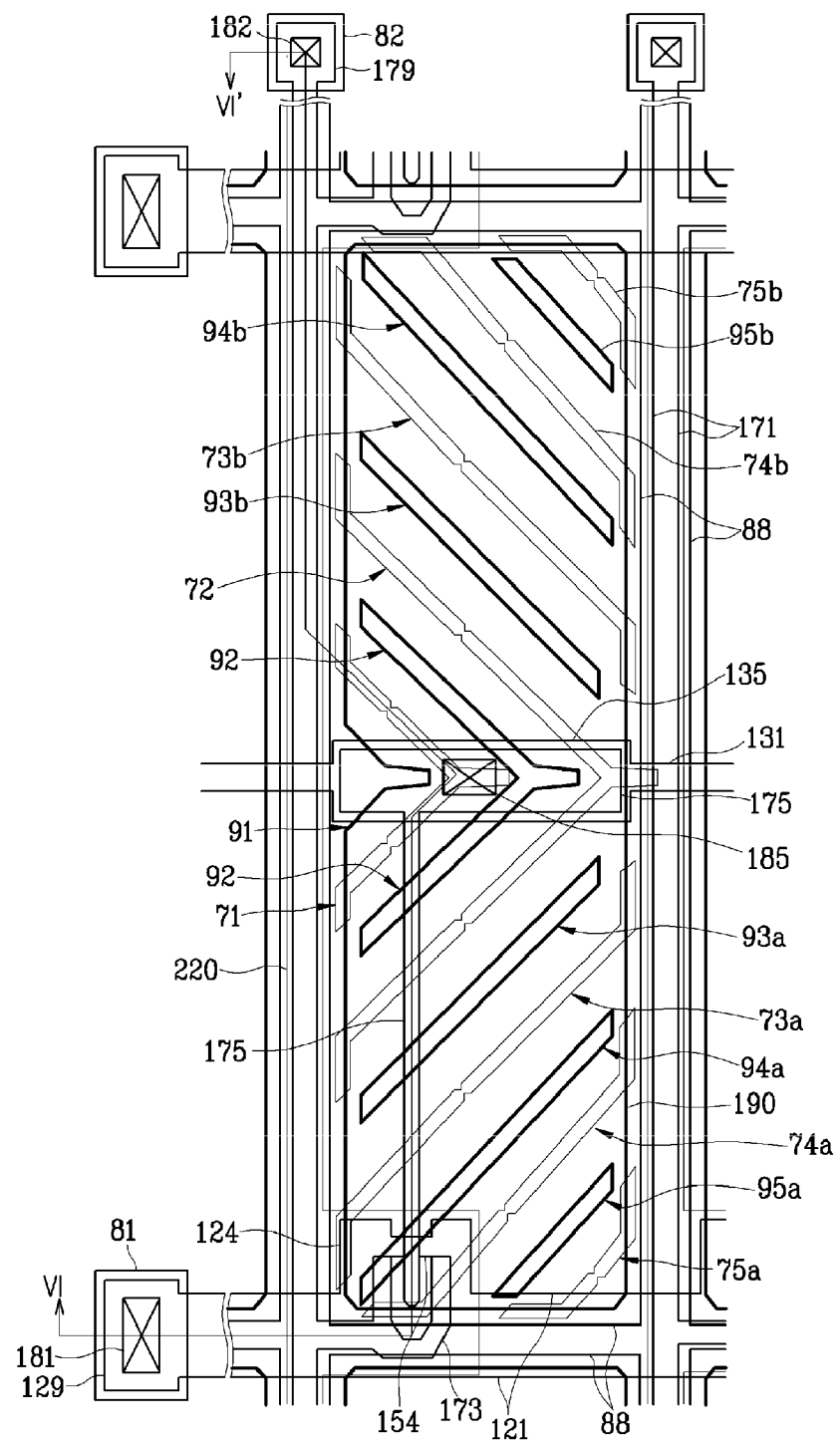
FIG. 27 is a layout view of an LCD according to another embodiment of the present invention.
Figure 28:
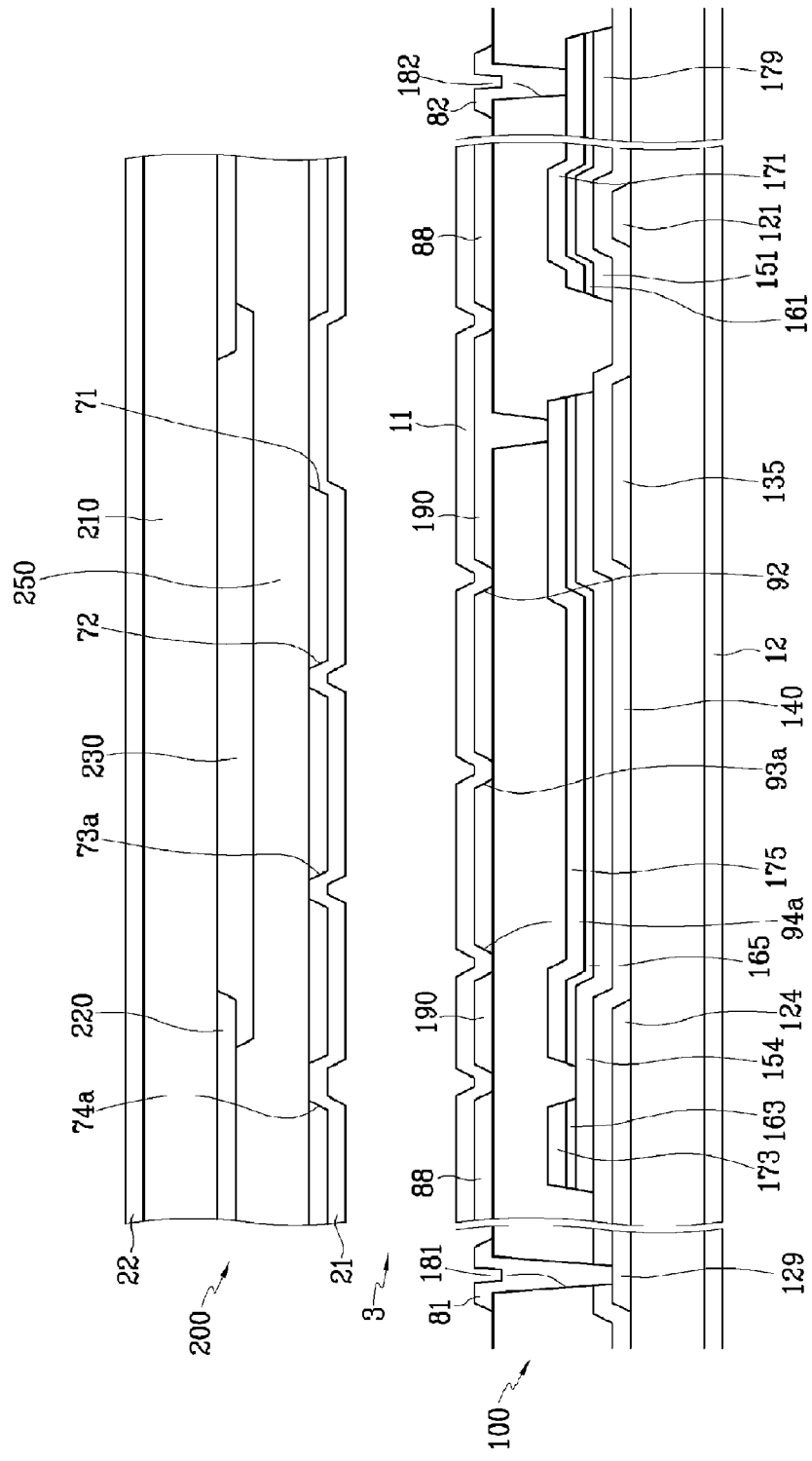
FIG. 28 is a sectional view of the LCD shown in FIG. 27 taken along the lines XXVIII-XXVIII'.

FIG. 27 is a layout view of an LCD according to another embodiment of the present invention and FIG. 28 is a sectional view of the LCD shown in FIG. 27 taken along the lines XXVIII-XXVIII'.

Referring to FIGS. 27 and 28, an LCD according to this embodiment also includes a TFT array panel 100, a common electrode panel 200, a LC layer 3 interposed therebetween, and a pair of polarizers 11 and 21 attached to outer surfaces of the panels 100 and 200.

Layered structures of the panels 100 and 200 according to this embodiment are almost the same as those shown in FIGS. 23-26.

Regarding the TFT array panel 100, a plurality of gate lines 121 including gate electrodes 124 and a plurality of storage electrode lines 131 including storage electrodes 135 are formed on a substrate 110, and a gate insulating layer 140, a plurality of semiconductors 151, and a plurality of ohmic contacts 161 and 165 are sequentially formed thereon. A plurality of data lines 171 including source electrodes 173 and a plurality of drain electrodes 175 are formed on the ohmic contacts 161 and 165, and a passivation layer 180 is formed thereon. A plurality of contact holes 181, 182 and 185 are provided at the passivation layer 180 and the gate insulating layer 140. A plurality of pixel electrodes 190, a plurality of shielding electrodes 88, and a plurality of contact assistants 81 and 82 are formed on the passivation layer 180 and an alignment layer 11 is coated thereon.

Regarding the common electrode panel 200, a light blocking member 220, a plurality of color filters 230, an overcoat 250, a common electrode 270, and an alignment layer 21 are formed on an insulating substrate 210.

Different from the LCD shown in FIGS. 23-26, the semiconductors 151 have almost the same planar shapes as the data lines 171 and the drain electrodes 175 as well as the underlying ohmic contacts 161 and 165. However, the semiconductors 151 include some exposed portions, which are not covered with the data lines 171 and the drain electrodes 175, such as portions located between the source electrodes 173 and the drain electrodes 175.

A manufacturing method of the TFT array panel according to an embodiment simultaneously forms the data lines 171, the drain electrodes 175, the semiconductors 151, and the ohmic contacts 161 and 165 using one photolithography process. Therefore, the manufacturing process is simplified by omitting a photolithography step.

Many of the above-described features of the LCD shown in FIGS. 23-26 may be appropriate to the LCD shown in FIGS. 27 and 28.

As describe above, the shielding electrodes 88 supplied with the common voltage that are disposed on the data lines 171 eliminate the electric field therebetween to remain the initial orientations of the LC molecules 310 such that the light leakage between the pixel electrodes 190 can be reduced. In addition, the shielding electrodes 88 reduce the parasitic capacitance between the data lines 171 and the pixel electrodes 190 and they block electric fields near the data lines 171 such that the distortion of the voltage of the pixel electrodes 190 and the signal delay of the data voltages transmitted by the data lines 171. In addition, the shielding electrodes 88 make the total parasitic capacitance nearly uniform to improve the image quality and to reduce the stitch defect.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A thin film transistor array panel comprising:
a gate line;
a data line intersecting the gate line;
a thin film transistor connected to the gate line and the data line;
a passivation layer formed on the data line;
a pixel electrode formed on the passivation layer and connected to the thin film transistor; and
a shielding electrode formed on the passivation layer,
wherein the shielding electrode is formed on the same layer as the pixel electrode,
wherein the shielding electrode extends along the data line and substantially fully covers the data line, and an edge of the pixel electrode parallel to the data line is disposed adjacent to an edge of the shielding electrode with an entire gap between the adjacent edges of the pixel electrode and the shielding electrode narrower than a width of the pixel electrode, and
wherein the entire gap between the adjacent edges of the pixel electrode and the shielding electrode is substantially uniform.

2. The thin film transistor array panel of claim 1, wherein the passivation layer comprises an organic insulator.

3. The thin film transistor array panel of claim 2, wherein the passivation layer comprises a color filter.

4. The thin film transistor array panel of claim 1, further comprising;
a storage electrode line overlapping the pixel electrode,
wherein the storage electrode line and the shielding electrode are electrically connected to each other.

5. The thin film transistor array panel of claim 1, wherein the pixel electrode has a chamfered edge.

6. The thin film transistor array panel of claim 5, wherein a length of the chamfered edge of the pixel electrode is equal to about four to ten microns.

7. The thin film transistor array panel of claim 1, wherein the pixel electrode has a cutout.

8. The thin film transistor array panel of claim 1, wherein the data line comprises a straight portion and a curved portion, the straight portion intersecting the gate line.

9. The thin film transistor array panel of claim 8, wherein the pixel electrode is curved along the curved portion of the data line.

10. A liquid crystal display comprising:
a first panel including a gate line,
a data line intersecting the gate line,
a thin film transistor connected to the gate line and the data line,
a passivation layer formed on the data line, a pixel electrode formed on the passivation layer and connected to the thin film transistor, a shielding electrode formed on the passivation layer, wherein the shielding electrode is formed on the same layer as the pixel electrode, and wherein the shielding electrode extends along the data and substantially fully covers the data line, and an entire gap between the shielding electrode and the pixel electrode is narrower than the width of the data line.

11. The liquid crystal display of claim 10, further comprising:

a second panel facing the first panel and including a common electrode formed thereon, wherein the common electrode and the shielding electrode are supplied with substantially the same voltage.

12. The liquid crystal display of claim 11, wherein the common electrode and the shielding electrode receive the same voltage being electrically connected to each other.

13. The liquid crystal display of claim 12, further comprising:

a storage electrode line overlapping the pixel electrode, wherein the storage electrode line is electrically connected to the common electrode.

14. The liquid crystal display of claim 10, further comprising a liquid crystal layer that is disposed between the first panel and the second panel, has negative anisotropy, and is subjected to a vertical alignment.

15. The liquid crystal display of claim 14, further comprising a tilt direction determining member having cutouts for determining tilt direction of liquid crystal molecules in the liquid crystal layer.

16. The liquid crystal display of claim 15, wherein the tilt direction determining member comprises a cutout of at least one of the pixel electrode and the common electrode or a protrusion disposed on at least one the pixel electrode and the common electrode.

17. The liquid crystal display of claim 14, further comprising a pair of crossed polarizers disposed on the first and the second panels.

18. The thin film transistor array panel of claim 4, wherein the storage electrode line is substantially parallel to the gate line.

19. The liquid crystal display of claim 13, wherein the storage electrode line is substantially parallel to the gate line.

* * * * *